(12) United States Patent
Liang et al.

(10) Patent No.: US 7,068,842 B2
(45) Date of Patent: Jun. 27, 2006

(54) SYSTEM AND METHOD FOR OBJECT IDENTIFICATION AND BEHAVIOR CHARACTERIZATION USING VIDEO ANALYSIS

(75) Inventors: Yiqing Liang, Vienna, VA (US); Linda Crnic, Denver, CO (US); Vikrant Kobla, Ashburn, VA (US); Wayne Wolf, Princeton, NJ (US)

(73) Assignee: CleverSys, Inc., Reston, VA (US)

( * ) Notice: Subject to any disclaimer, the term of this patent is extended or adjusted under 35 U.S.C. 154(b) by 266 days.

(21) Appl. No.: 10/666,741

(22) Filed: Sep. 19, 2003

(65) Prior Publication Data
US 2004/0131254 A1 Jul. 8, 2004

Related U.S. Application Data

(63) Continuation of application No. 09/718,374, filed on Nov. 24, 2000, now Pat. No. 6,678,413.

(51) Int. Cl.
*G06K 9/00* (2006.01)

(52) U.S. Cl. .................. 382/181; 382/103; 348/143

(58) Field of Classification Search .......... 382/103, 382/106, 107, 108, 110, 115, 154, 181, 194, 382/199, 203, 216, 224, 287, 294, 305, 318, 382/190, 282, 285; 119/421; 128/897; 348/143; 340/573.1; 702/139
See application file for complete search history.

(56) References Cited

U.S. PATENT DOCUMENTS

| | | | | |
|---|---|---|---|---|
| 3,974,798 A | * | 8/1976 | Meetze, Jr. | 119/421 |
| 4,337,726 A | * | 7/1982 | Czekajewski et al. | 119/421 |
| 4,574,734 A | * | 3/1986 | Mandalaywala et al. | 119/421 |
| 5,816,256 A | * | 10/1998 | Kissinger et al. | 128/897 |
| 5,870,138 A | * | 2/1999 | Smith et al. | 348/143 |
| 6,072,903 A | * | 6/2000 | Maki et al. | 382/190 |
| 6,535,131 B1 | * | 3/2003 | Bar-Shalom et al. | 340/573.1 |
| 6,601,010 B1 | * | 7/2003 | Fowler et al. | 702/139 |

* cited by examiner

*Primary Examiner*—Kanjibhai Patel
*Assistant Examiner*—Seyed Azarian
(74) *Attorney, Agent, or Firm*—White & Case LLP

(57) ABSTRACT

In general, the present invention is directed to systems and methods for finding the position and shape of an object using video. The invention includes a system with a video camera coupled to a computer in which the computer is configured to automatically provide object segmentation and identification, object motion tracking (for moving objects), object position classification, and behavior identification. In a preferred embodiment, the present invention may use background subtraction for object identification and tracking, probabilistic approach with expectation-maximization for tracking the motion detection and object classification, and decision tree classification for behavior identification. Thus, the present invention is capable of automatically monitoring a video image to identify, track and classify the actions of various objects and the object's movements within the image. The image may be provided in real time or from storage. The invention is particularly useful for monitoring and classifying animal behavior for testing drugs and genetic mutations, but may be used in any of a number of other surveillance applications.

37 Claims, 16 Drawing Sheets

SYSTEM AND METHOD FOR OBJECT IDENTIFICATION AND BEHAVIOR CHARACTERIZATION USING VIDEO ANALYSIS

This is a continuation application of application Ser. No. 09/718,374, filed on November 24, 2000, which is issued on Jan. 13, 2004 as U.S. Pat. No. 6,678,413.

GOVERNMENT RIGHTS NOTICE

Portions of the material in this specification arose as a result of Government support under contracts MH58964 and MH58964-02 between Clever Sys., Inc. and The National Institute of Mental Health, National Institute of Health. The Government has certain rights in this invention.

BACKGROUND OF THE INVENTION

1. Technical Field

The invention relates generally to object identification and recognition. More particularly, one aspect of the invention is directed to monitoring and characterization of an object in an image, for example an animal or a person, using video analysis.

2. Background Art

Video analysis has developed over the past few decades to become an integral part of machine operations in manufacturing using machine automation. For example, video object recognition and pattern recognition has been used to orient and align various pieces of a product for machining and assembly in various manufacturing industries. One such use is in the manufacturing of semiconductor integrated circuits and microelectronic packaging. In this case, pattern recognition has made great inroads because the size of the work product is microscopic and orientation and alignment of the work product is thus far too tedious for a human being to do consistently and accurately over a large number of pieces.

In recent years, military has carried out research to use video to track moving targets such as tanks and vehicles, in the scene. Other positioning instruments such as global positioning system will be used to assist such tracking.

Another application for video analysis is monitoring animal activity in laboratory testing for the pharmaceutical and biological sciences. One particular area is monitoring animal behavior to determine the effects of various new drugs or gene changes on a particular type of animal. One such animal used in laboratory testing is the mouse.

Over the last two decades, major technological advances have enabled scientists to build a rich repository of mouse models. Model organisms are an important tool for understanding and dissecting human disease and biological process. Because mice and humans share many of the same fundamental biological and behavioral processes, this animal is one of the most significant laboratory models for human disease and studying biological processes in mammals. However, the adequate behavioral characterization (behavioral phenotyping—the impact of a genetic manipulation on visible characteristics of an organism) of genetically engineered mice is becoming a serious bottleneck in the development of animal models; an exponentially increasing number of genotypes are created, but the behavioral phenotyping is often at best rudimentary or is abandoned completely. This is because presently the phenotyping process is largely manual, time consuming, and insensitive to subtle phenotypes.

Video technologies for mouse behavior analysis have been introduced and several products are commercially available. However, these technologies are still primitive and the functionality of the products is far from adequate for the research purposes. There are presently two types of systems available for monitoring mouse behavior, those that identify individual behaviors and those that identify only the location of the mouse.

The most basic state-of-art mouse behavior analysis systems rely on traditional analog technologies that can only treat a mouse as an indivisible object and identify the mouse location. All the information about a mouse is packed as a point in the space and a lot of important information about mouse behavior is lost. The best these systems can do is to find the position of the mouse. Systems like San Diego Instruments' Photobeam and AccuScan Instruments Inc.'s Digiscan Line of Animal Activity Monitoring, Columbus, Ohio uses simple and rudimentary photo-beams to detect and track the positions of mouse. These systems trackers have a very low spatial resolution, limiting their output to a rough measure of the animal's activity. They cannot differentiate even such basic behaviors as locomotion and circling. Adding a time line for the locus of mouse point is all they can offer. Other animal location type systems used to monitor animal motion include those described in U.S. Pat. Nos. 3,100,473; 3,803,571; 3,974,798; 4,337,726; 4,574,734; and 5,816,256.

The other systems in the field are the systems that identify individual behavior using video. The existing video analysis systems (e.g. Noldus Observer/Ethovision, Sterling, Vir.; HVS Image, Hampton, UK; AccuScan Instruments Inc.'s VideoScan2000 System; and San Diego Instruments Poly-Track system, San Diego, Calif.) do not meet expectations either. Digitized images from video are used to capture the body of mouse and provide quantitative data about the position and movements of the animal and the pattern of these variables across time. They do not just treat the animal (e.g., mouse) as a point in the space. Instead, they handle it as a block of pixels. More information is preserved. However, they can only make use of a few simple features. For example, the mass center of the animal (e.g., mouse) is calculated and used as a means for tracking the animal (e.g., a mouse). As such, a lot of information that is critical to identify the animal's behaviors such as different postures, positions of portions of the animal's body such as limbs, is lost. These systems can only distinguish basic behaviors such as locomotion, and cannot automatically identify simple animal postures such as eating, rearing, and jumping, not to mention complex behaviors such as skilled reaching. Such behavior identification requires human intervention and input.

In addition, these systems are often developed for rats that remain relatively stationary in shape as they are in locomotion. However, other animals such as a mouse frequently stretch out, making their center of mass much less stable than a rat. As the center of gravity shifts rapidly and frequently, this falsely adds to measures such as distance traveled, making these systems highly inaccurate for mice. Further, the systems are devised to study white rats on a dark background and are not accurate for tracking other animals such as brown or black mice.

The most advanced systems are those offered by Noldus. The Noldus Observer system has a video camera, TV monitor, a high end VCR, and a PC system, all hooked together. The camera takes video footage of the mouse in a cage. This video is recorded on videotape, digitized, input into the PC system, and displayed on the computer monitor.

Although the human observer can control the recorded video that is displayed, the human observer still needs to look at the animal on the screen, decide which behavior the animal is engaged in, and enter (by typing) the information into a mechanism provided by the system for storage and later analysis. While this system facilitates observation of behavior, it does not automate it, and is thus prone to human error and extremely labor intensive. The tasks of coding behavior throughout the day and building a profile of behavior for different types of animals and different strains of the same animal (e.g., different strains of mouse) is prohibitively time consuming with this equipment.

SUMMARY OF THE INVENTION

In general, the present invention is directed to systems and methods for finding patterns of behaviors and/or activities of an object using video. The invention includes a system with a video camera connected to a computer in which the computer is configured to automatically provide object identification, object motion tracking (for moving objects), object shape and posture classification, and behavior identification. Thus, the present invention is capable of automatically monitoring a video image to identify, track and classify the actions of various objects and their movements. The video image may be provided in real time from a camera and/or from a storage location. The invention is particularly useful for monitoring and classifying animal behavior for testing drugs and genetic mutations, but may be used in any of a number of surveillance or other applications.

In one embodiment the invention includes a system in which an analog video camera and a video record/playback device (e.g., VCR) are coupled to a video digitization/compression unit. The video camera may provide a video image containing an object to be identified. The video digitization/compression unit is coupled to a computer that is configured to automatically monitor the video image to identify, track and classify the actions of the object and its movements over time within a sequence of video session image frames. The digitization/compression unit may convert analog video and audio into, for example, MPEG or other formats. The computer may be, for example, a personal computer, using either a Windows platform or a Unix platform, or a MacIntosh computer and compatible platform. The computer is loaded and configured with custom software programs (or equipped with firmware) using, for example, MATLAB or C/C++ programming language, so as to analyze the digitized video for object identification and segmentation, tracking, and/or behavior/activity characterization. This software may be stored in, for example, a program memory, which may include ROM, RAM, CD ROM and/or a hard drive, etc. In one variation of the invention the software (or firmware) includes a unique background subtraction method which is more simple, efficient, and accurate than those previously known.

In operation, the system receives incoming video images from either the video camera in real time or pre-recorded from the video record/playback unit. If the video is in analog format, then the information is converted from analog to digital format and may be compressed by the video digitization/compression unit. The digital video images are then provided to the computer where various processes are undertaken to identify and segment a predetermined object from the image. In a preferred embodiment the object is an object (e.g., a mouse) in motion with some movement from frame to frame in the video, and is in the foreground of the video images. In any case, the digital images may be processed to identify and segregate a desired (predetermined) object from the various frames of incoming video. This process may be achieved using, for example, background subtraction, mixture modeling, robust estimation, and/or other processes.

The shape and location of the desired object is then tracked from one frame or scene to another frame or scene of video images. Next, the changes in the shapes, locations, and/or postures of the object of interest may be identified, their features extracted, and classified into meaningful categories, for example, vertical positioned side view, horizontal positioned side view, vertical positioned front view, horizontal positioned front view, moving left to right, etc. Then, the shape, location, and posture categories may be used to characterize the object's activity into one of a number of pre-defined behaviors. For example, if the object is an animal, some pre-defined normal behaviors may include sleeping, eating, drinking, walking, running, etc., and pre-defined abnormal behavior may include spinning vertical, jumping in the same spot, etc. The pre-defined behaviors may be stored in a database in the data memory. The behavior may be characterized using, for example, approaches such as rule-based label analysis, token parsing procedure, and/or Hidden Markov Modeling (HMM). Further, the system may be constructed to characterize the object behavior as new behavior and particular temporal rhythm.

In another preferred embodiment directed toward video analysis of animated objects such as animals, the system operates as follows. As a preliminary matter, normal postures and behaviors of the animals are defined and may be entered into a Normal Postures and Behaviors database. In analyzing in a first instant, incoming video images are received. The system determines if the video images are in analog or digital format and input into a computer. If the video images are in analog format they are digitized and may be compressed, using, for example, an MPEG digitizer/compression unit. Otherwise, the digital video image may be input directly to the computer. Next, a background may be generated or updated from the digital video images and foreground objects detected. Next, the foreground objects features are extracted. Then, the foreground object shape is classified into various categories, for example, standing, sitting, etc. Next, the foreground object posture is compared to the various predefined postures stored in the database, and then identified as a particular posture or a new (unidentified) posture. Then, various groups of postures are concatenated into a series to make up a foreground object behavior and then compared against the sequence of postures, stored in for example a database in memory, that make up known normal or abnormal behaviors of the animal. The abnormal behaviors are then identified in terms of known abnormal behavior, new behavior and/or daily rhythm.

In one variation of the invention, object detection is performed through a unique method of background subtraction. First, the incoming digital video signal is split into individual images (frames) in real-time. Then, the system determines if the background image derived from prior incoming video needs to be updated due to changes in the background image or a background image needs to be developed because there was no background image was previously developed. If the background image needs to be generated, then a number of frames of video image, for example 20, will be grouped into a sample of images. Then, the system creates a standard deviation map of the sample of images. Next, the process removes a bounding box area in each frame or image where the variation within the group of images is above a predetermined threshold (i.e., where the object of interest or moving objects are located). Then, the various images within the sample less the bounding box area are averaged. Final background is obtained by averaging 5–10 samples. This completes the background generation process. However, often the background image does not remain constant for a great length of time due to various reasons. Thus, the background needs to be recalculated periodically as above or it can be recalculated by keeping track of the difference image and note any sudden changes. The newly generated background image is next subtracted from the current video image(s) to obtain foreground areas that may include the object of interest.

Next, the object identification/detection process is performed. First, regions of interest (ROI) are obtained by identifying areas where the intensity difference generated from the subtraction is greater than a predetermined threshold, which constitute potential foreground object(s) being sought. Classification of these foreground regions of interest will be performed using the sizes of the ROIs, distances among these ROIs, threshold of intensity, and connectedness, to thereby identify the foreground objects. Next, the foreground object identification/detection process may be refined by adaptively learning histograms of foreground ROIs and using edge detection to more accurately identify the desired object(s), Finally, the information identifying the desired foreground object is output. The process may then continue with the tracking and/or behavior characterization step(s).

The previous embodiments are particularly applicable to the study and analysis of mice used in genetic and drug experimentation. One variation of the present invention is directed particularly to automatically determining the behavioral characteristics of a mouse in a home cage. The need for sensitive detection of novel phenotypes of genetically manipulated or drug-administered mice demands automation of analyses. Behavioral phenotypes are often best detected when mice are unconstrained by experimenter manipulation. Thus, automation of analysis of behavior in a known environment, for example a home cage, would be a powerful tool for detecting phenotypes resulting from gene manipulations or drug administrations. Automation of analysis would allow quantification of all behaviors as they vary across the daily cycle of activity. Because gene defects causing developmental disorders in humans usually result in changes in the daily rhythm of behavior, analysis of organized patterns of behavior across the day may also be effective in detecting phenotypes in transgenic and targeted mutant mice. The automated system may also be able to detect behaviors that do not normally occur and present the investigator with video clips of such behavior without the investigator having to view an entire day or long period of mouse activity to manually identify the desired behavior.

The systematically developed definition of mouse behavior that is detectable by the automated analysis according to the present invention makes precise and quantitative analysis of the entire mouse behavior repertoire possible for the first time. The various computer algorithms included in the invention for automating behavior analysis based on the behavior definitions ensure accurate and efficient identification of mouse behaviors. In addition, the digital video analysis techniques of the present invention improves analysis of behavior by leading to: (1) decreased variance due to non-disturbed observation of the animal; (2) increased experiment sensitivity due to the greater number of behaviors sampled over a much longer time span than ever before possible; and (3) the potential to be applied to all common normative behavior patterns, capability to assess subtle behavioral states, and detection of changes of behavior patterns in addition to individual behaviors.

Development activities have been completed to validate various scientific definitions of mouse behaviors and to create novel digital video processing algorithms for mouse tracking and behavior recognition, which are embodied in a software and hardware system according to the present invention. An automated method for analysis of mouse behavior from digitized 24 hour video has been achieved using the present invention and its digital video analysis method for object identification and segmentation, tracking, and classification. Several different methods and their algorithms, including Background Subtraction, Probabilistic approach with Expectation-Maximization, and Robust Estimation to find parameter values by best fitting a set of data measurements and results proved successful. The entire behavioral repertoire of individual mice in their home cage was categorized using successive iterations by manual videotape analysis. These manually defined behavior categories constituted the basis of automatic classification. Classification criteria (based on features extracted from the foreground object such as shape, position, movement) were derived and fitted into a decision tree (DT) classification algorithm. The decision tree could classify almost 500 sample features into 5 different postures classes with an accuracy over 93%. A simple HMM system has been built using dynamic programming and has been used to classify the classified postures identified by the DT and yields an almost perfect mapping from input posture to output behaviors in mouse behavior sequences.

The invention may identify some abnormal behavior by using video image information (for example, stored in memory) of known abnormal animals to build a video profile for that behavior. For example, video image of vertical spinning while hanging from the cage top was stored to memory and used to automatically identify such activity in mice. Further, abnormalities may also result from an increase in any particular type of normal behavior. Detection of such new abnormal behaviors may be achieved by the present invention detecting, for example, segments of behavior that do not fit the standard profile. The standard profile may be developed for a particular strain of mouse whereas detection of abnormal amounts of a normal behavior can be detected by comparison to the statistical properties of the standard profile.

Thus, the automated analysis of the present invention may be used to build profiles of the behaviors, their amount, duration, and daily cycle for each animal, for example each commonly used strain of mice. A plurality of such profiles may be stored in, for example, a database in a data memory of the computer. One or more of these profile may then be compared to a mouse in question and difference from the profile expressed quantitatively.

The techniques developed with the present invention for automation of the categorization and quantification of all home-cage mouse behaviors throughout the daily cycle is a powerful tool for detecting phenotypic effects of gene manipulations in mice. As previously discussed, this technology is extendable to other behavior studies of animals and humans, as well as surveillance purposes. As will be described in detail below, the present invention provides automated systems and methods for automated accurate identification, tracking and behavior categorization of an object whose image is captured with video.

DESCRIPTION OF THE PREFERRED EMBODIMENTS

Figure 1:
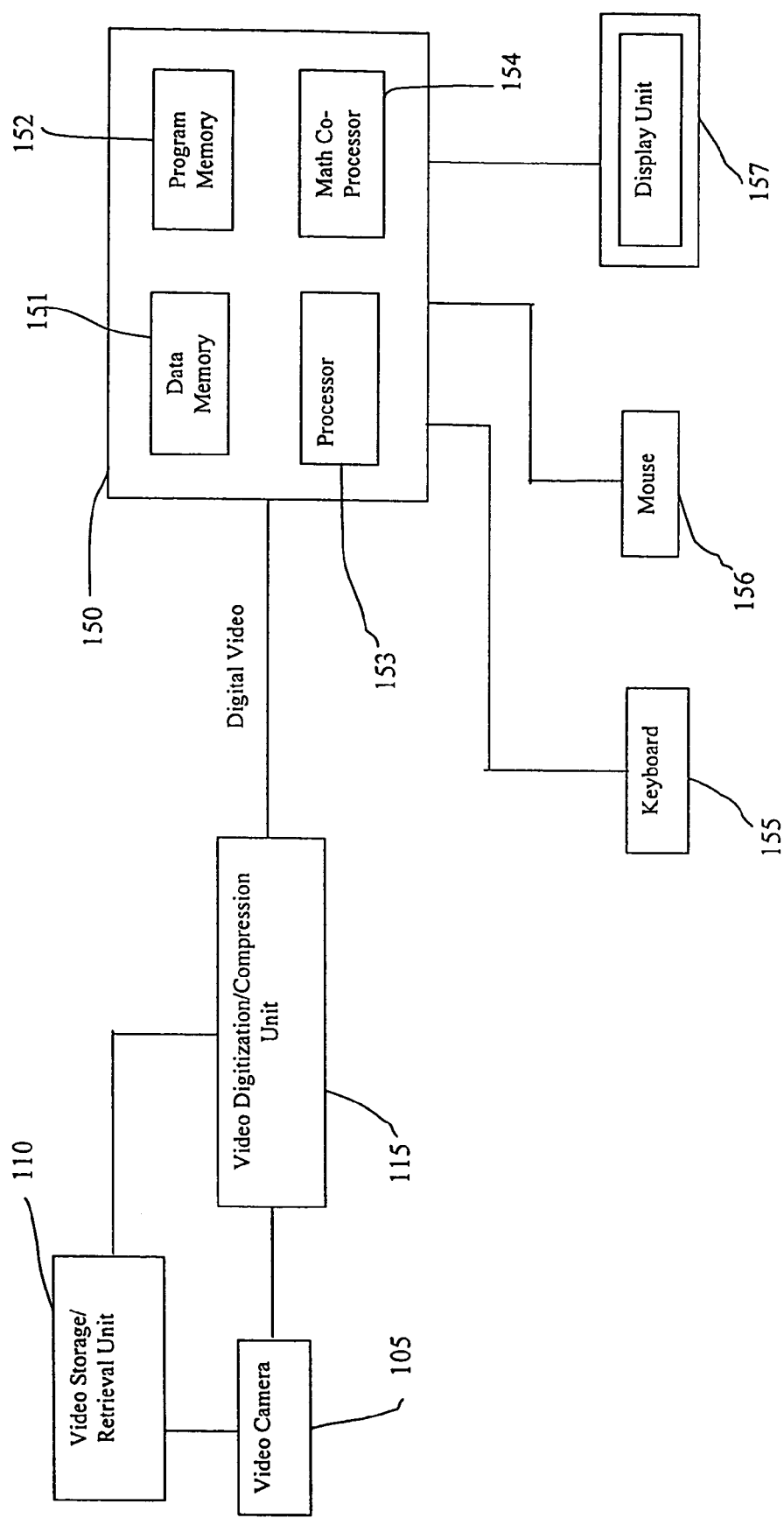
FIG. 1 is a block diagram of one exemplary system configurable to find the position, shape, and behavioral characteristics of an object using automated video analysis, according to one embodiment of the present invention.

The past few years have seen an increase in the integration of video camera and computer technologies. Today, the integration of the two technologies allows video images to be digitized, stored, and viewed on small inexpensive computers, for example, a personal computer. Further, the processing and storage capabilities of these small inexpensive computers has expanded rapidly and reduced the cost for performing data and computational intensive applications. Thus, video analysis systems may now be configured to provide robust surveillance systems that can provide automated analysis and identification of various objects and characterization of their behavior. The present invention provides such systems and related methods.

In general, the present invention can automatically find the patterns of behaviors and/or activities of a predetermined object being monitored using video. The invention includes a system with a video camera connected to a computer in which the computer is configured to automatically provide object identification, object motion tracking (for moving objects), object shape and posture classification, and behavior identification. In a preferred embodiment the system includes various video analysis algorithms. The computer processes analyze digitized video with the various algorithms so as to automatically monitor a video image to identify, track and classify the actions of one or more predetermined objects and its movements captured by the video image as it occurs from one video frame or scene to another. The system may characterize behavior by accessing a database of object information of known behavior of the predetermined object. The image to be analyzed may be provided in real time from one or more camera and/or from storage.

In various exemplary embodiments described in detail as follows, the invention is configured to enable monitoring and classifying of animal behavior that results from testing drugs and genetic mutations on animals. However, as indicated above the system may be similarly configured for use in any of a number of surveillance or other applications. For example, the invention can be applied to various situations in which tracking moving objects is needed. One such situation is security surveillance in public areas like airports, military bases, or home security systems. The system may be useful in automatically identifying and notifying proper law enforcement officials if a crime is being committed and/or a particular behavior being monitored is identified. The system may be useful for monitoring of parking security or moving traffic at intersections so as to automatically identify and track vehicle activity. The system may be configured to automatically determine if a vehicle is speeding or has performed some other traffic violation. Further, the system may be configured to automatically identify and characterize human behavior involving guns or human activity related to robberies or thefts. Similarly, the invention may be capable of identifying and understanding subtle behaviors involving portions of body such as forelimb and can be applied to identify and understand human gesture recognition. This could help deaf individuals communicate. The invention may also be the basis for computer understanding of human gesture to enhance the present human-computer interface experience, where gestures will be used to interface with computers. The economic potential of applications in computer-human interface applications and in surveillance and monitoring applications is enormous.

In one preferred embodiment illustrated in FIG. 1, the invention includes a system in which an analog video camera 105 and a video storage/retrieval unit 110 may be coupled to each other and to a video digitization/compression unit 115. The video camera 105 may provide a real time video image containing an object to be identified. The video storage/retrieval unit 110 may be, for example, a VCR, DVD, CD or hard disk unit. The video digitization/compression unit 115 is coupled to a computer 150 that is configured to automatically monitor a video image to identify, track and classify the actions (or state) of the object and its movements (or stillness) over time within a sequence of images. The digitization/compression unit 115 may convert analog video and audio into, for example, MPEG format, Real Player format, etc. The computer may be, for example, a personal computer, using either a Windows platform or a Unix platform, or a MacIntosh computer and compatible platform. In one variation the computer may include a number of components such as (1) a data memory 151, for example, a hard drive or other type of volatile or non-volatile memory; (2) a program memory 152, for example, RAM, ROM, EEPROM, etc. that may be volatile or non-volatile memory; (3) a processor 153, for example, a microprocessor; and (4) a second processor to manage the computation intensive features of the system, for example, a math coprocessor 154. The computer may also include a video processor such as an MPEG encoder/decoder. Although the computer 150 has been shown in FIG. 1 to include two memories (data memory 151 and program memory 152) and two processors (processor 153 and math co-processor 154), in one variation the computer may include only a single processor and single memory device or more then two processors and more than two memory devices. Further, the computer 150 may be equipped with user interface components such as a keyboard 155, electronic mouse 156, and display unit 157.

In one variation, the system may be simplified by using all digital components such as a digital video camera and a digital video storage/retrieval unit 110, which may be one integral unit. In this case, the video digitization/compression unit 115 may not be needed.

The computer is loaded and configured with custom software program(s) (or equipped with firmware) using, for example, MATLAB or C/C++ programming language, so as to analyze the digitized video for object identification and segmentation, tracking, and/or behavior/activity characterization. This software may be stored in, for example, a program memory 152 or data memory that may include ROM, RAM, CD ROM and/or a hard drive, etc. In one variation of the invention the software (or firmware) includes a unique background subtraction method which is more simple, efficient, and accurate than those previously known which will be discussed in detail below. In any case, the algorithms may be implemented in software and may be understood as unique functional modules as shown in FIG. 2 and now described.

Figure 2:
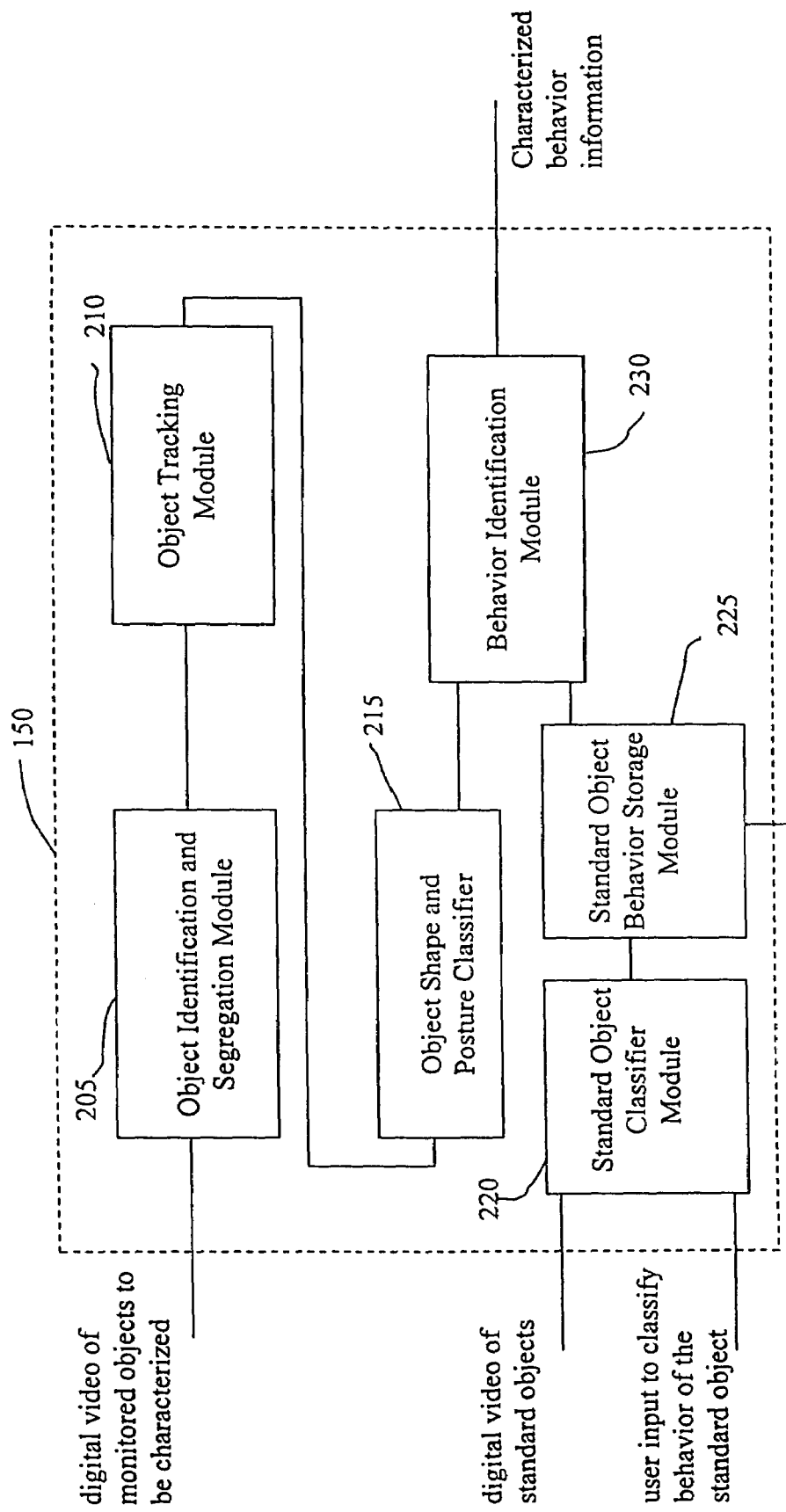
FIG. 2 is a block diagram of various functional portions of a computer system, such as the computer system shown in FIG. 1, when configured to find the position, shape, and behavioral characteristics of an object using automated video analysis, according to one embodiment of the present invention.

Referring to FIG. 2, the system is preloaded with standard object information before analyzing an incoming video including a predetermined object, for example, a mouse. First, a stream of digital video including a known object with known characteristics may be fed into the system to a standard object classifier module 220. A user may then view the standard object on a screen and identify and classify various behaviors of the standard object, for example, standing, sitting, lying, normal, abnormal, etc. Data information representing such standard behavior may then be stored in the standard object behavior storage modules 225, for example a database in data memory 151. Of course, standard object behavior information data sets may be loaded directly into the standard object behavior storage module 225 from another system or source as long as the data is compatible with the present invention protocols and data structure. In any case, once the standard object behavior data is entered into the standard object behavior storage module 225, the system may be used to analyze and classify the behavior of one or more predetermined objects, for example, a mouse.

In the automatic video analysis mode, digital video (either real-time and/or stored) of monitored objects to be identified and characterized is input to an object identification and segregation module 205. This module identifies and segregates a predetermined type of object from the digital video image and inputs it to an object tracking module 210. The object tracking module 210 facilitates tracking of the predetermined object from one frame or scene to another as feature information. This feature information is then extracted and input to the object shape and posture classifier 215. This module classifies the various observed states of the predetermined object of interest into various shape and posture categories and sends it to the behavior identification module 230. The behavior identification module 230 compares the object shape, motion, and posture information with shape, motion, and posture information for a standard object and classifies the behavior accordingly into the predefined categories exhibited by the standard object, including whether the behavior is normal, abnormal, new, etc. This information is output to the user as characterized behavior information on, for example, a display unit 157.

Figure 3:
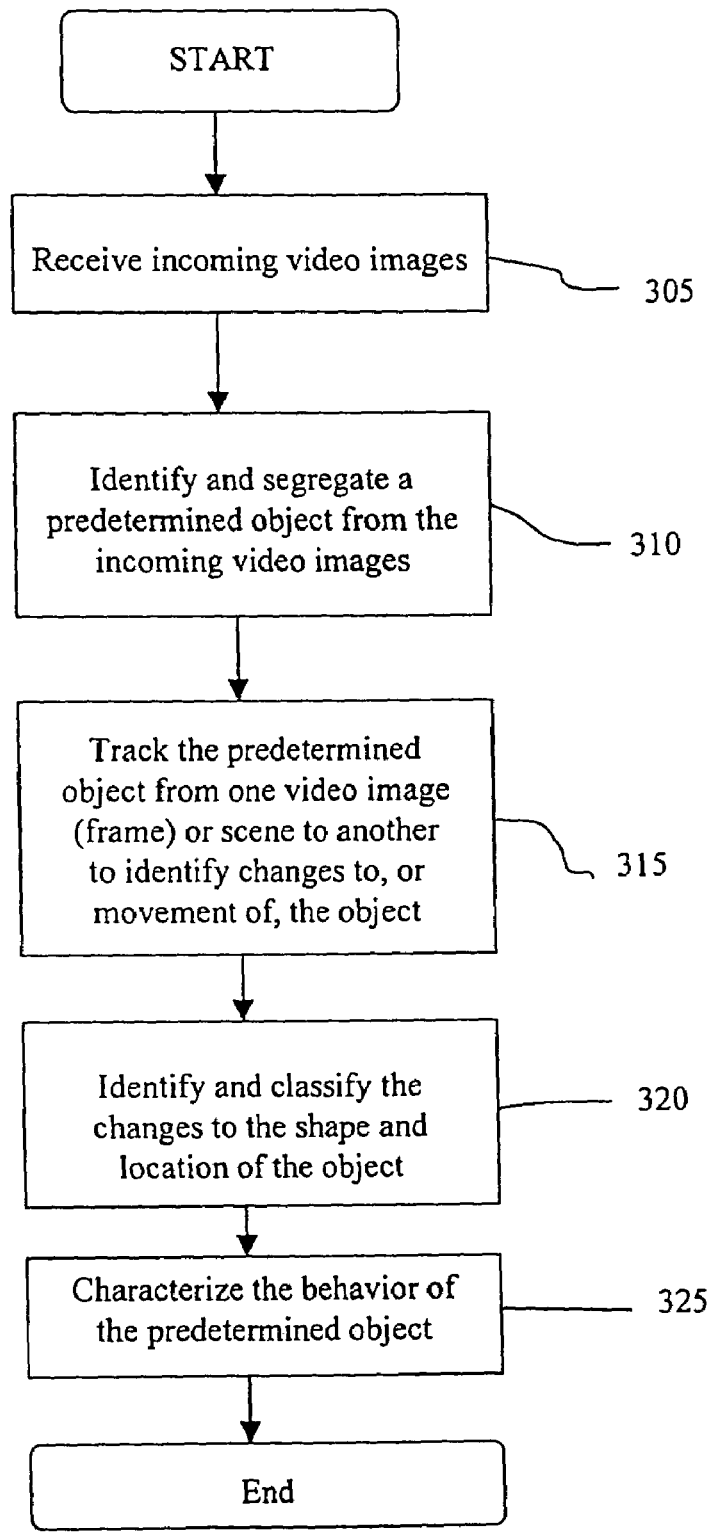
FIG. 3 is a flow chart of a method of automatic video analysis for object identification and characterization, according to one embodiment of the present invention.

Referring now to FIG. 3, a general method of operation for one embodiment of the invention will be described. In operation, in the video analysis mode the system may receive incoming video images at step 305, from the video camera 105 in real time, pre-recorded from the video storage/retrieval unit 110, and/or a memory integral to the computer 150. If the video is in analog format, then the information is converted from analog to digital format and may be compressed by the video digitization/compression unit 115. The digital video images are then provided to the computer 150 for various computational intensive processing to identify and segment a predetermined object from the image. In a preferred embodiment, the object to be identified and whose activities is to be characterized is a moving object, for example a mouse, which has some movement from frame to frame or scene to scene in the video images and is generally in the foreground of the video images. In any case, at step 310 the digital images may be processed to identify and segregate a desired (predetermined) object from the various frames of incoming video. This process may be achieved using, for example, background subtraction, mixture modeling, robust estimation, and/or other processes.

Next, at step 315, various movements (or still shapes) of the desired object may then be tracked from one frame or scene to another frame or scene of video images. As will be discussed in more detail below, this tracking may be achieved by, for example, tracking the outline contour of the object from one frame or scene to another as it varies from shape to shape and/or location to location. Next, at step 320, the changes in the motion of the object, such as the shapes, locations, and postures of the object of interest, may be identified and their features extracted and classified into meaningful categories. These categories may include, for example, vertical positioned side view, horizontal positioned side view, vertical positioned front view, horizontal positioned front view, moving left to right, etc. Then, at step 325, the states of the object, for example the shape, location, and posture categories, may be used to characterize the objects activity into one of a number of pre-defined behaviors. For example, if the object is an animal, some pre-defined normal behaviors may include sleeping, eating, drinking, walking, running, etc., and pre-defined abnormal behavior may include spinning vertical, jumping in the same spot, etc. The pre-defined behaviors may be stored in a database in the data memory 151.

Types of behavior may also be characterized using, for example, approaches such as rule-based label analysis, token parsing procedure, and/or Hidden Markov Modeling (HMM). The HMM is particularly helpful in characterizing behavior that is determined with temporal relationships of the various motion of the object across a selection of frames. From these methods, the system may be capable of characterizing the object behavior as new behavior and particular temporal rhythm.

Figure 4:
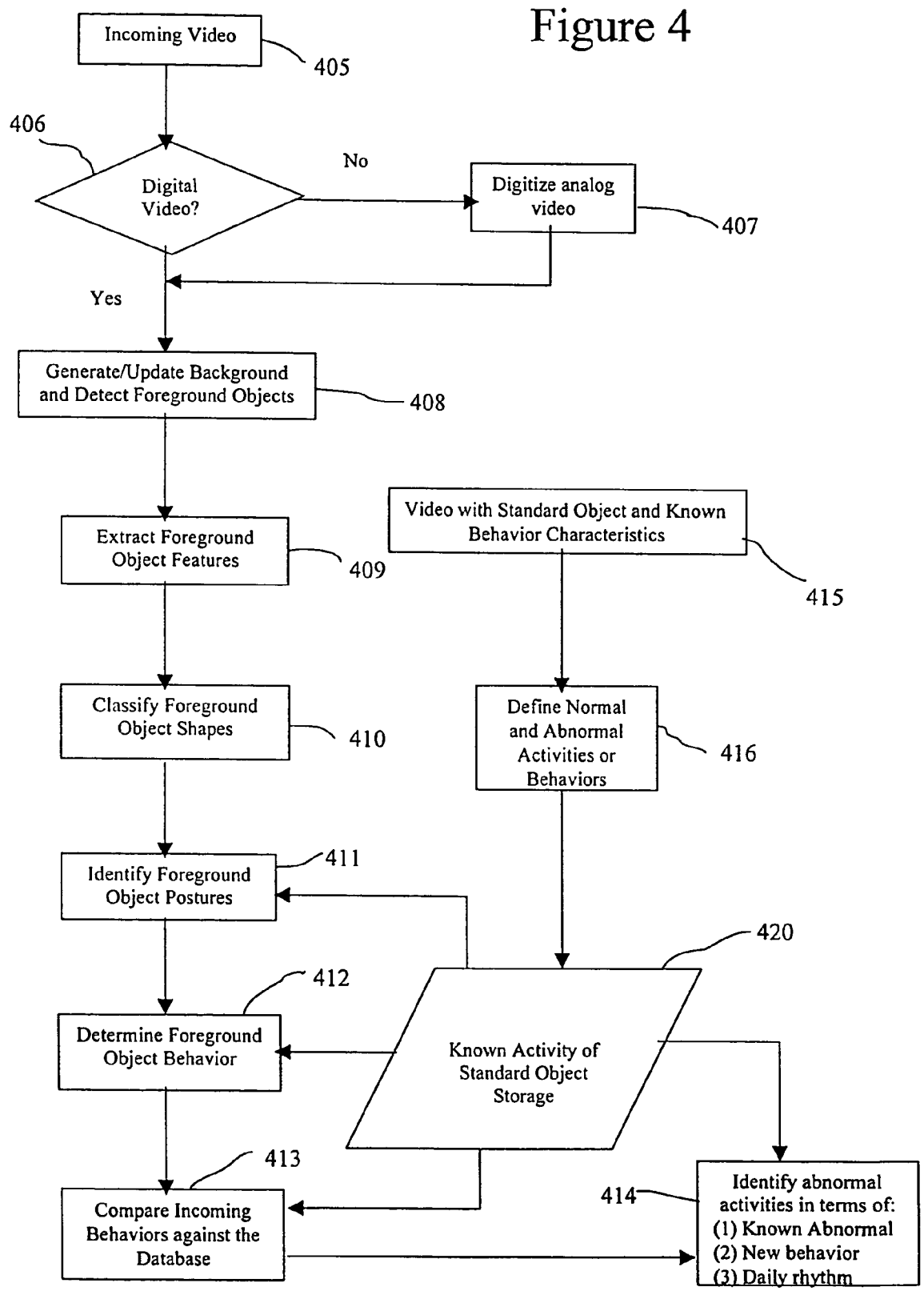
FIG. 4 is a flow chart of a method of automatic video analysis for object identification and characterization, according to another embodiment of the present invention.

Referring now to FIG. 4 a more detailed description of another preferred embodiment will be described. In this case the system is directed toward video analysis of animated objects such as animals. As a preliminary matter, at step 415 video of the activities of a standard object and known behavior characteristics are input into the system. This information may be provided from a video storage/retrieval unit 110 in digitized video form into a standard object classified module 220. This information may then be manually categorized at step 416 to define normal and abnormal activities or behaviors by a user viewing the video images on the display unit 157 and inputting their classifications. For example, experts in the field may sit together watching recorded scenes. They may then define, for example, an animal's (e.g., a mouse) behavior(s), both qualitatively and quantitatively, with or without some help from systems like the Noldus Observer system. These cataloged behaviors may constitute the important posture and behavior database and are entered into a storage, for example a memory, of known activity of the standard object at step 420. This information provides a point of reference for video analysis to characterize the behavior of non-standard objects whose behaviors/activities need to be characterized such as genetically altered or drug administered mice. For example, normal postures and behaviors of the animals are defined and may be entered into a normal postures and behaviors database.

Once information related to characterizing a standard object (s) is established, the system may then be used to analyze incoming video images that may contain an object for which automated behavior characterization is desired. First, at step 405, incoming video images are received. Next, at decision step 406, the system determines if the video images are in analog or digital format. If the video images are in analog format they are then digitized at step 407. The video may be digitized and may be compressed, using, for example, a digitizer/compression unit 115 into a convenient digital video format such as MPEG, RealPlayer, etc. Otherwise, the digital video image may be input directly to the computer 150. Now the object of interest is identified within the video images and segregated for analysis. As such, at step 408, a background may be generated or updated from the digital video images and foreground objects including a predetermined object for behavior characterization may be detected. For example, a mouse in a cage is detected in the foreground and segregated from the background. Then, at step 409, features such as centroid, the principal orientation angle of the object, the area (number of pixels), the eccentricity (roundness), and the aspect ratio of the object, and/or shape in terms of convex hull or b-spline, of the foreground object of interest (e.g., a mouse) are extracted. Next, at step 410, the foreground object shape and postures are classified into various categories, for example, standing, sitting, etc.

Then, at step 411, the foreground object (e.g., a mouse) posture may be compare to the various predefined postures in the set of known postures in the standard object storage of step 420, which may be included in a database. At steps 412, the observed postures of the object contained in the analyzed video image may be classified and identified as a particular posture known for the standard object or a new previously unidentified posture. Next, at step 413, various groups of postures may be concatenated into a series to make up a foreground object behavior that is then compared against the sequence of postures, stored in for example a database in memory, that make up a known standard object behavior. This known standard behavior is, in a preferred embodiment, normal behavior for the type of animal being studied. However, the known activity of the standard object may be normal or abnormal behavior of the animal. In either case, at step 414, the abnormal behaviors are then identified in terms of (1) known abnormal behavior; (2) new behavior likely to be abnormal; and/or (3) daily rhythm differences likely to be abnormal behavior. Known normal behavior may also be output as desired by the user. This information is automatically identified to the user for their review and disposition. In one variation of the invention, the information output may include behavior information that is compatible with current statistical packages such as Systat and SPSS.

Figure 5:
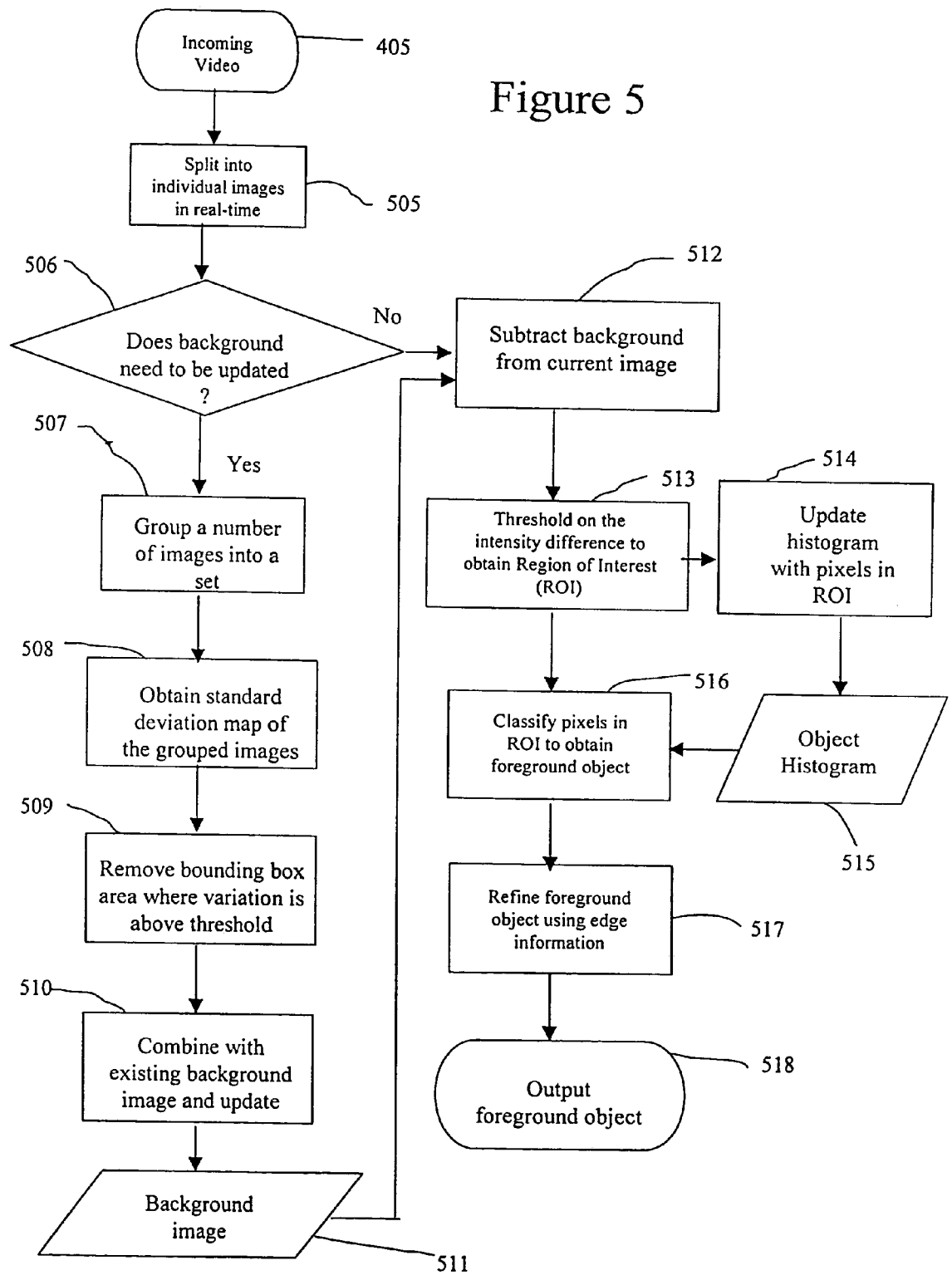
FIG. 5 is a flow chart of a method of automatic video analysis for object detection and identification, according to one variation of the present invention.

In one embodiment of the invention as illustrated in FIG. 5, object detection is performed through a unique method of background subtraction. First, at step 405, incoming video is provided to the system for analysis. This video may be provided by digital equipment and input to the object identification and segregation module 205 of the computer 150. Next, at step 505, the incoming digital video signal may be split into individual images (frames) in real-time. This step may be included if it is desired to carry out real-time analysis. Then, at decision step 506, the system determines if the background image needs to be developed because there was no background image developed previously or the background image has changed. If the background image needs to be generated or updated, then at step 507 a background image is generated by first grouping a number of frames or images into a sample of video images, for example 20 frames or images. The background may need to be updated periodically due to changes caused by, for example, lighting and displacement of moveable objects in the cage, such as the bedding. Then, at step 508 the system generates a standard deviation map of the group of images. Next, at step 509, an object(s) bounding box area is identified and removed from each frame or image to create a modified frame or image. The bounding box area is determined by sensing the area wherein the variation of a feature such as the standard deviation of intensity is above a predetermined threshold. Thus, an area in the digitized video image where the object of interest in motion is located is removed leaving only a partial image. Then, at step 510, the various modified images within the group, less the bounding box area, are combined, for example averaged, to create a background image at step 511.

Since varying pixels are not used in averaging, "holes" will be created in each image that is being used in the averaging process. Over time, not all frames will have these holes at the same location and hence, a complete background image is obtained after the averaging process. Final background is obtained by averaging 5–10 samples. This completes at least one iteration of the background generation process.

The background image does not remain constant for a great length of time due to various reasons. For example, the bedding in a mouse cage can shift due to the activity of the mouse. External factors such as change in illumination conditions also require background image recalculations. If the camera moves, then, background might need to be changed. Thus, the background typically needs to be recalculated periodically as described above or it can be recalculated by keeping track of the difference image and note any sudden changes such as an increase in the number of particular color (e.g., white) pixels in the difference image or the appearance of patches of the particular color (e.g., white) pixels in another area of the difference image. In any case, the newly generated background image may then be combined with any existing background image to create a new background image at step 511.

The newly generated background image is next, at step 512, subtracted from the current video image(s) to obtain foreground areas that may include the object of interest. Further, if the background does not need to be updated as determined at decision step 506, then the process may proceed to step 512 and the background image is subtracted from the current image, leaving the foreground objects.

Next, at steps 513–518, the object identification/detection process is performed. First, at step 513, regions of interest (ROI) are obtained by identifying an area where the intensity difference is greater than a predetermined threshold, which constitute potential foreground object(s) being sought. Classification of these foreground regions of interest will be performed using the sizes of the ROIs, distances among these ROIs, threshold of intensity, and connectedness to identify the foreground objects. Next, the foreground object identification/detection process may be refined by utilizing information about the actual distribution (histograms) of the intensity levels of the foreground object and using edge detection to more accurately identify the desired object(s).

At step 514, during both the background generation and background subtraction steps for object identification, the system continuously maintains a distribution of the foreground object intensities as obtained. A lower threshold may be used to thereby permit a larger amount of noise to appear in the foreground image in the form of ROIs. Thus, at step 514, a histogram is then updated with the pixels in the ROI. At step 515, plotting a histogram of all the intensities of a particular color pixels over many images, provides a bimodal shape with the larger peak corresponding to the foreground object's intensity range and the smaller peak corresponding to the noise pixels in the ROI's images. Now, at step 516, having "learned" the intensity range of the foreground object, only those pixels in the foreground object that conform to this intensity range are selected, thereby identifying the foreground object more clearly even with background that is fairly similar.

In any case, next at step 517 the foreground object of interest may be refined using edge information to more accurately identify the desired object. An edge detection mechanism such as Prewitt operator is applied to the original image. Adaptive thresholds for edge detections can be used. Once the edge map is obtained, the actual boundary of the foreground object is assumed to be made up of one or more segments in the edge map, i.e., the actual contour of the foreground objects comprises edges in the edge map. The closed contour of the "detected" foreground object is broken into smaller segments, if necessary. Segments in the edge map that are closest to these contour segments according to a distance metric are found to be the desired contour. One exemplary distance metric is the sum of absolute normal distance to the edge map segment from each point in the closed contour of the "detected" foreground object. Finally, at step 518 the information identifying the desired foreground object is output. The process may then continue with tracking and/or behavior characterization steps.

The previous embodiments are generally applicable to identifying, tracking, and characterizing the activities of a particular object of interest present in a video image, e.g., an animal, a human, a vehicle, etc. However, the invention is also particularly applicable to the study and analysis of animals used for testing new drugs and/or genetic mutations. As such, a number of variations of the invention related to determining changes in behavior of mice will be described in more detail below using examples of video images obtained.

One variation of the present invention is designed particularly for the purpose of automatically determining the behavioral characteristics of a mouse. The need for sensitive detection of novel phenotypes of genetically manipulated or drug-administered mice demands automation of analyses. Behavioral phenotypes are often best detected when mice are unconstrained by experimenter manipulation. Thus, automation of analysis of behavior in a home cage would be a preferred means of detecting phenotypes resulting from gene manipulations or drug administrations. Automation of analysis as provided by the present invention will allow quantification of all behaviors and may provide analysis of the mouse's behavior as they vary across the daily cycle of activity. Because gene defects causing developmental disorders in humans usually result in changes in the daily rhythm of behavior, analysis of organized patterns of behavior across the day may be effective in detecting phenotypes in transgenic and targeted mutant mice. The automated system of the present invention may also detect behaviors that do not normally occur and present the investigator with video clips of such behavior without the investigator having to view an entire day or long period of mouse activity to manually identify the desired behavior.

The systematically developed definition of mouse behavior that is detectable by the automated analysis of the present invention makes precise and quantitative analysis of the entire mouse behavior repertoire possible for the first time. The various computer algorithms included in the invention for automating behavior analysis based on the behavior definitions ensure accurate and efficient identification of mouse behaviors. In addition, the digital video analysis techniques of the present invention improves analysis of behavior by leading to: (1) decreased variance due to non-disturbed observation of the animal; (2) increased experiment sensitivity due to the greater number of behaviors sampled over a much longer time span than ever before possible; and (3) the potential to be applied to all common normative behavior patterns, capability to assess subtle behavioral states, and detection of changes of behavior patterns in addition to individual behaviors. Development activities have been complete to validate various scientific definition of mouse behaviors and to create novel digital video processing algorithms for mouse tracking and behavior recognition, which are embody in software and hardware system according to the present invention.

Various lighting options for videotaping have been evaluated. Lighting at night as well as with night vision cameras was evaluated. It has been determined that good quality video was obtained with normal commercial video cameras using dim red light, a frequency that is not visible to rodents. Videos were taken in a standard laboratory environment using commercially available cameras 105, for example a Sony analog camera, to ensure that the computer algorithms developed would be applicable to the quality of video available in the average laboratory. The commercially available cameras with white lighting gave good results during the daytime and dim red lighting gave good results at night time.

Referring again to FIG. 3, the first step in the analysis of home cage behavior is an automated initialization step that involves analysis of video images to identify the location and outline of the mouse, as indicated by step 310. Second, the location and outline of the mouse are tracked over time, as indicated by step 315. Performing the initialization step periodically may be used to reset any propagation errors that appear during the tracking step. As the mouse is tracked over time, its features including shape are extracted, and used for training and classifying the posture of the mouse from frame to frame, as indicated by step 320. Posture labels are generated for each frame, which are analyzed over time to determine the actual behavior, as indicated by step 325. These steps will now be described in detail using the particular application of mouse behavior characterization.

I. Mouse Identification

Figure 6:
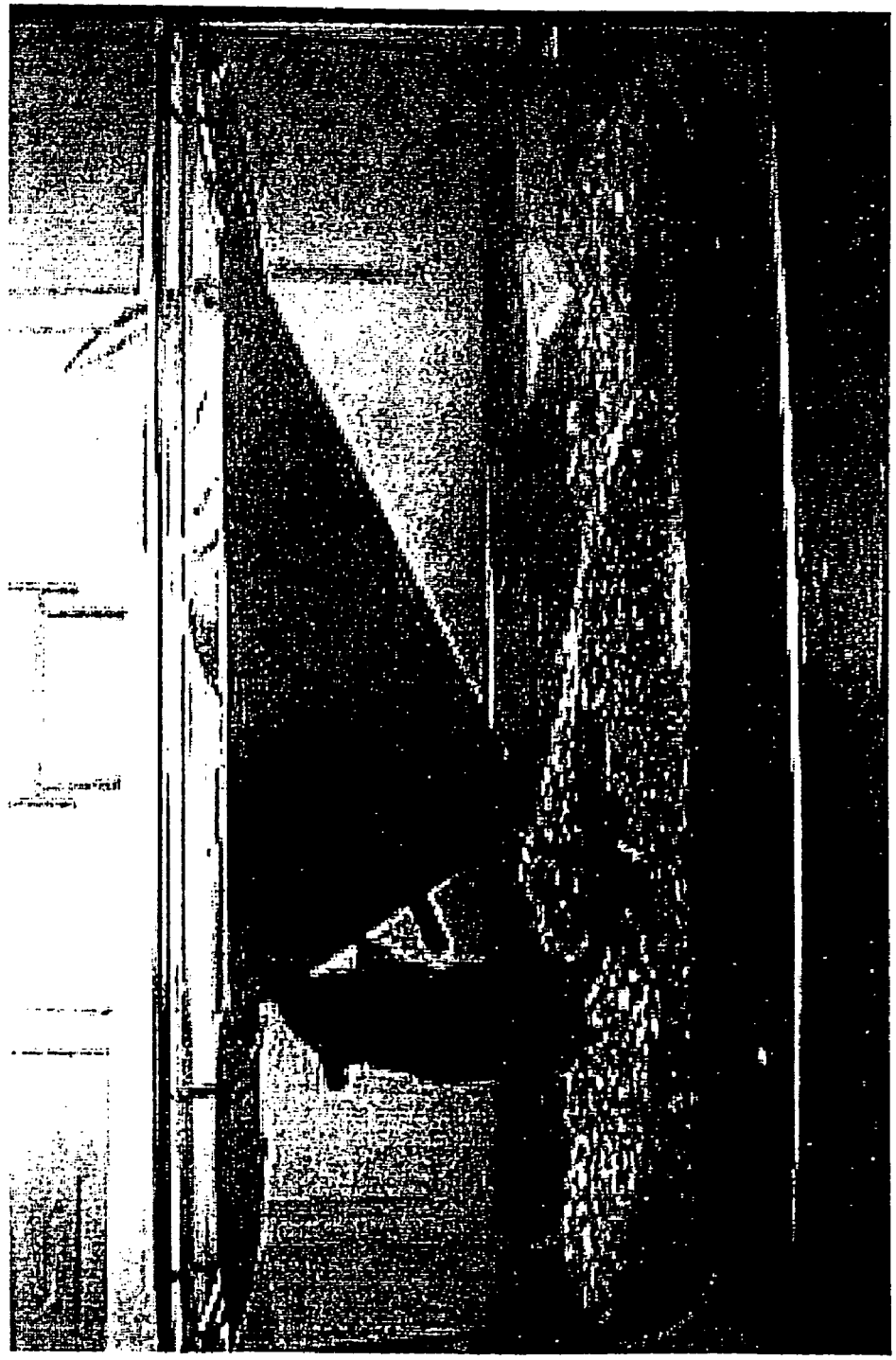
FIG. 6 illustrates a sample video image frame with a mouse in a rearing up posture as determined using one variation of the present invention to monitor and characterize mouse behavior.

A typical video frame of a mouse in its home cage is shown in FIG. 6. In this video frame a mouse is shown in a rearing up posture. Many such frames make up the video of, for example, a 24 hour mouse behavior monitoring session. As previously indicated, there are several approaches available for identifying and tracking moving objects in a scene. One of the simplest and most straightforward methods is background subtraction of which one example was provided in FIG. 5.

A. Background Subtraction

Background subtraction as used in the present invention generally involves generating a still background image from all or a subset of the frames in a video clip and subtracting this background image from any given image to obtain the foreground objects.

The background is generated by averaging many frames, for example approximately 100 frames of the video, after compensating for any shifts caused by the motion of the camera. Even if foreground objects are present in the frames that are being averaged to generate the background image, their unwanted contribution is negligible when large numbers of frames are used for the background calculation, assuming that the foreground object does not remain at the same location throughout. Nevertheless, it may be helpful to not consider those pixels where the foreground object is present.

In one implementation of the background averaging process, only the stationary pixels in an image are considered to avoid the unwanted contributions of the foreground moving objects. The stationary and non-stationary pixels are determined by analyzing the local variations of each pixel of a series of frames over a short time period as indicated in step 509 of FIG. 5. The standard deviation from the mean is first calculated for each pixel. If the standard deviation is greater than a chosen threshold, we tag those pixels as being non-stationary or varying pixels. Those pixels that are below the threshold may be tagged as stationary or constant pixels. Only those stationary pixels are used in the averaging process to calculate the background. Since the varying pixels are not used, there will be "holes" in each image that is being used in the averaging process. Over time, not all frames will have these holes at the same location and hence, a complete background image may be obtained with the averaging process. Once the background image has been obtained, subtraction of the background image from the given analyzed image yields the foreground objects. One exemplary algorithm for such a background subtraction method will now be described.

Let T be the number of frames that are being averaged to calculate the background. Let $p_{(x,y,t)}$ be the pixel value at position (x, y) and frame number t, then the mean, $\bar{p}_{(x,y)}$, and standard deviation, $\sigma_{(x,y)}$, for that location are defined respectively as, $$\bar{p}_{(x,y)} = \frac{1}{T}\sum_{t=1}^{T} p_{(x,y,t)}$$

$$\sigma^2_{(x,y)} = \frac{1}{T-1}\sum_{t=1}^{T} (p_{(x,y,t)} - \bar{p}_{(x,y)})^2$$

If the standard deviation, $\sigma_{(x,y)}$, for a particular pixel is greater than a threshold, for example an intensity of 64 on the scale of 0 to 255 was used for a video clip with mouse in a cage, then it is omitted from the background image calculation.

Typically, the background image of a video session does not remain constant for a great length of time. For example, in the case of monitoring mouse behavior the bedding in the mouse cage can shift due to the activity of the mouse. Hence, the background may need to be recalculated periodically. External factors such as change in illumination conditions may require background image recalculations. If the camera 105 moves, then the background image might need to be recalculated.

Another method, other than performing background recalculations periodically, is to keep track of the difference image and note any sudden changes such as an increase in the number of white pixels in the difference image or the appearance of patches of white pixels in another area of the difference image.

Figure 7A:
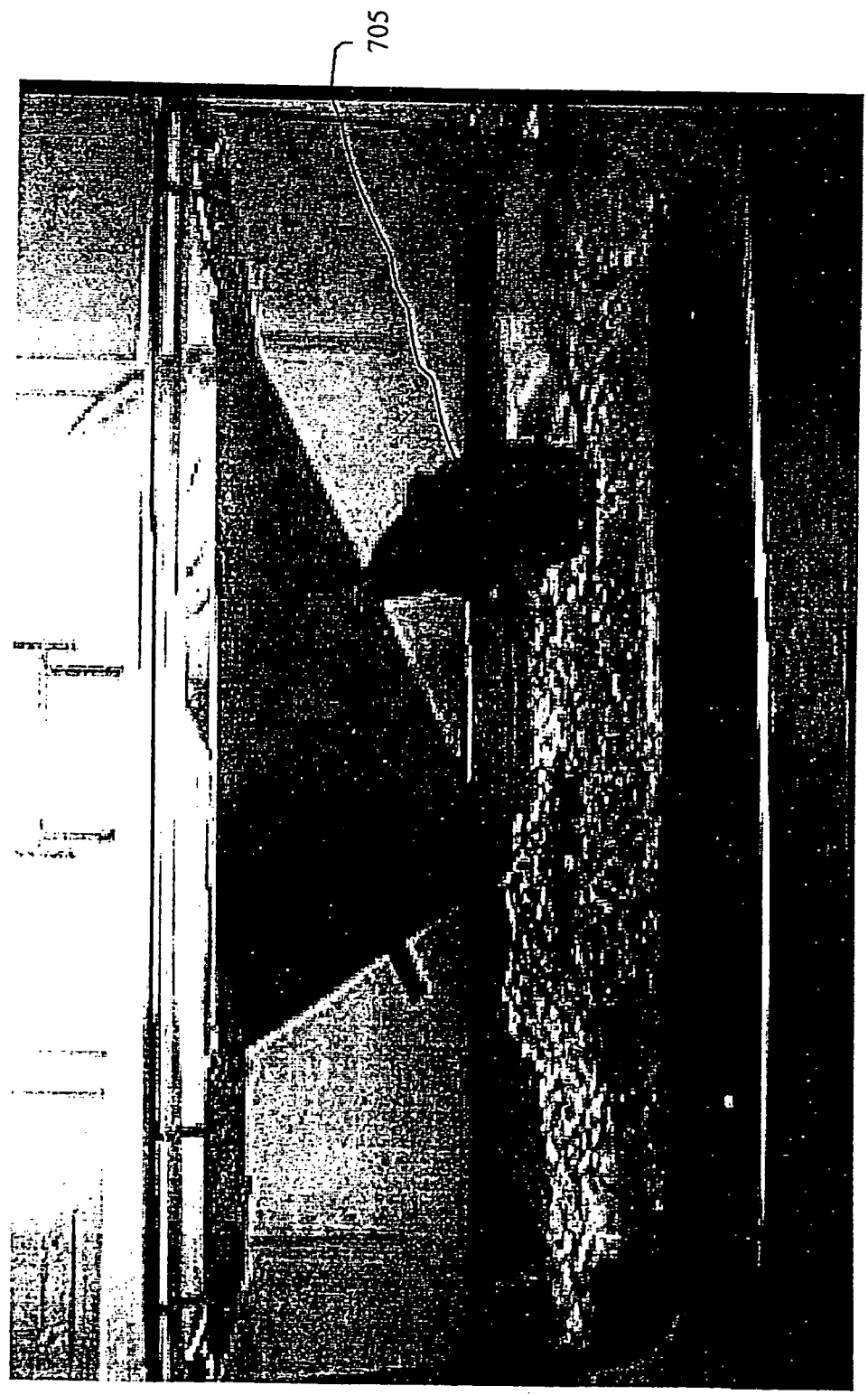
FIG. 7A is a first video image frame in a sequence with a mouse in an eating posture for illustrating background generation for a background subtraction process according to one variation of the present invention as applied for monitoring and characterizing mouse behavior.
Figure 7B:
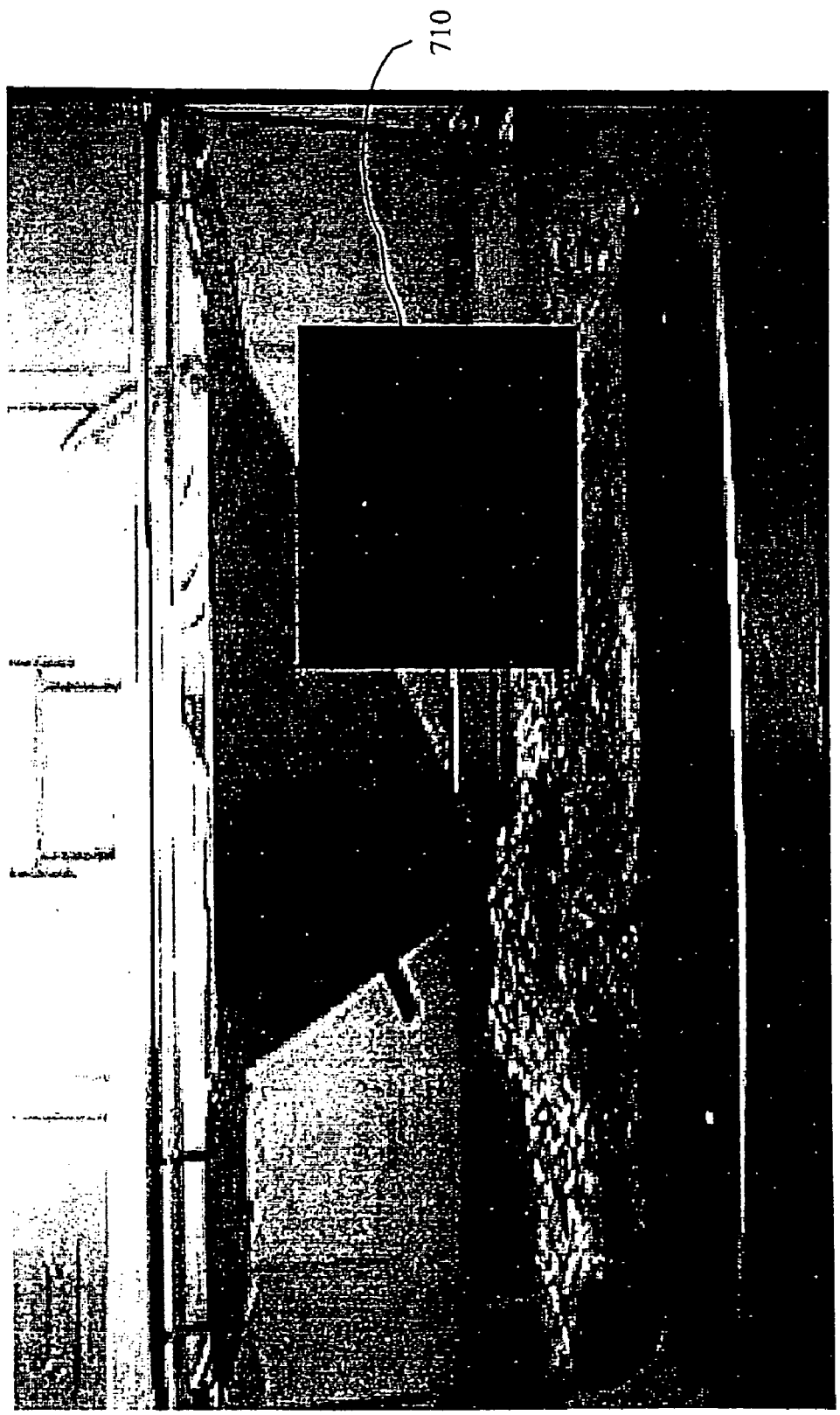
FIG. 7B is a copy of the first video image frame of FIG. 7A in which the process has extracted an area of the video image related to the mouse in the foreground resulting in a "hole" which will be filled up when other frames are averaged with it for a background subtraction process according to one variation of the present invention as applied for monitoring and characterizing mouse behavior.
Figure 7C:
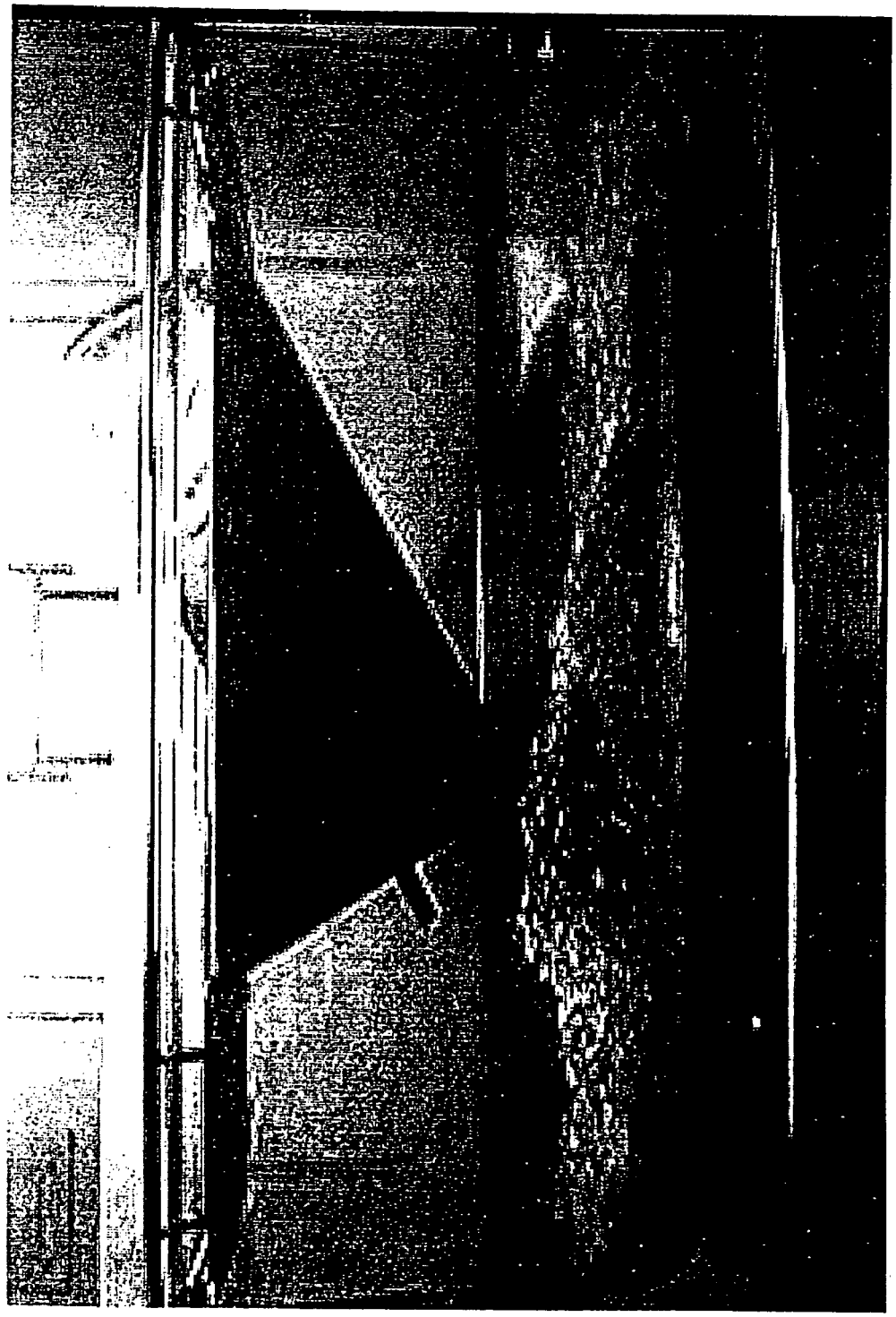
FIG. 7C is the resulting background image for a video clip including the first video image frame of FIG. 7A converted as shown in FIG. 7B and averaged with subsequent video images, according to one variation of the present invention as applied for monitoring and characterizing mouse behavior.

An example of some screen shots of one exemplary background subtraction process used for monitoring a mouse with the present invention is shown in FIGS. 7A, 7B and 7C. FIG. 7A illustrates a first frame in a sequence with the mouse in an eating posture 705. FIG. 7B illustrates the same frame of the video image now having the area of the frame in which the pixels are changing identified as a blocked out 710. As a result the background has a "hole" 710 (shown in black). This hole 710 will be filled with an image indicative of the true complete background image when other frames are averaged with it.

In order to generate a good background from a video sequence, several samples should first be generated. For example, a 10–20 frame sample (30 frames per second) from a video clip is taken and then averaged to generate one sample. Once a sample is obtained, it may be used to update a previously existing background. A sufficiently complete background may be obtained by averaging a number of sample sets, for example 5–10 samples sets. FIG. 7C illustrates the resulting background image for the video clip once the group of frames in a sample set and a number of sample sets are averaged together. As can be seen in FIG. 7C, this method is quite successful at generating a reasonably complete background image (less the foreground object of interest) to be used in the background subtraction process for identifying and segregating a desired object, in this case a mouse.

One primary advantage of this technique is its low complexity that enables the background recalculations and foreground object detection to be performed with ease. This makes the background subtraction method of the present invention well suited for use in real-time processing applications.

B. Other Algorithms for Mouse Identification

Various other algorithms may be used for object or mouse identification. For example, one might use a mixture model and/or robust estimation algorithms in addition to, or in place of, background subtraction. These algorithms are newly developed theory in image sequence processing and object segmentation. They may handle object segmentation better than background subtraction in certain circumstances. Preliminary analysis indicates that mixture model and/or robust estimation algorithms may have excellent results for mouse identification.

II. Location and Outline Identification and Feature Extraction

In any case, once the background has been generated, it is then used to determine the foreground objects by taking the intensity difference and applying a threshold determination procedure to remove noise. This step may involve threshold determination on both the intensity and the size of region. An 8-connection labeling procedure may be performed to screen out disconnected small noisy regions and improve the region that corresponds to the mouse. In the labeling process, all pixels in a frame will be assigned a label as foreground pixel or background pixel. Thresholding has generated labels for certain pixels. Neighbors of those labeled pixels that have not been labeled may obtain the same label as the labeled pixel. Eight-connectedness defines 8 corner-adjacent pixels that are all neighbors. The remaining regions indicated to be foreground objects are much smaller compared to the region of mouse, thus a size criteria is used to select the larger mouse region. The outline or contour of this foreground object is thus determined.

Further, the convex hull of the pixels is used in the foreground object for representation. Convex hull H of an arbitrary set S, which is a region in the frame in this case, is the smallest set containing S. The set difference H-S is called the convex deficiency D of the set S. The region S' boundary can be partitioned by following the contour of S and marking the points at which transition is made into or out of a component of the convex deficiency. These marking points can be connected into a polygon that gives a description of the region. The centroid (or center of mass) of the foreground object is calculated and is used for representing the location of the object (e.g., mouse).

Figure 8A:
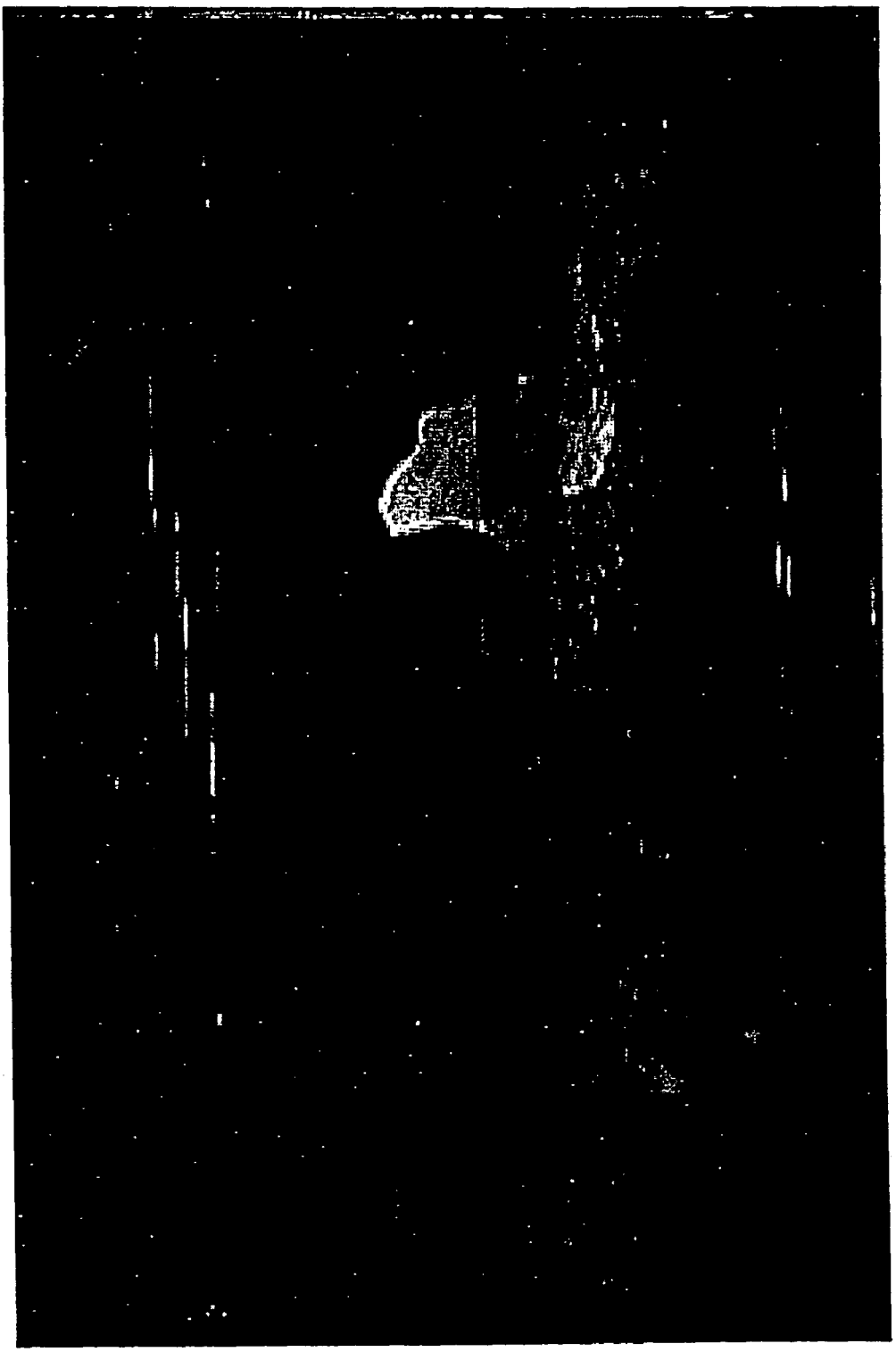
FIG. 8A is a difference image between foreground and background for the image shown in FIG. 7A, according to one variation of the present invention as applied for monitoring and characterizing mouse behavior.
Figure 8B:
FIG. 8B is the image shown in FIG. 7A after completing a threshold process for identifying the foreground image of the mouse which is shown as correctly identified, according to one variation of the present invention as applied for monitoring and characterizing mouse behavior.
Figure 8C:
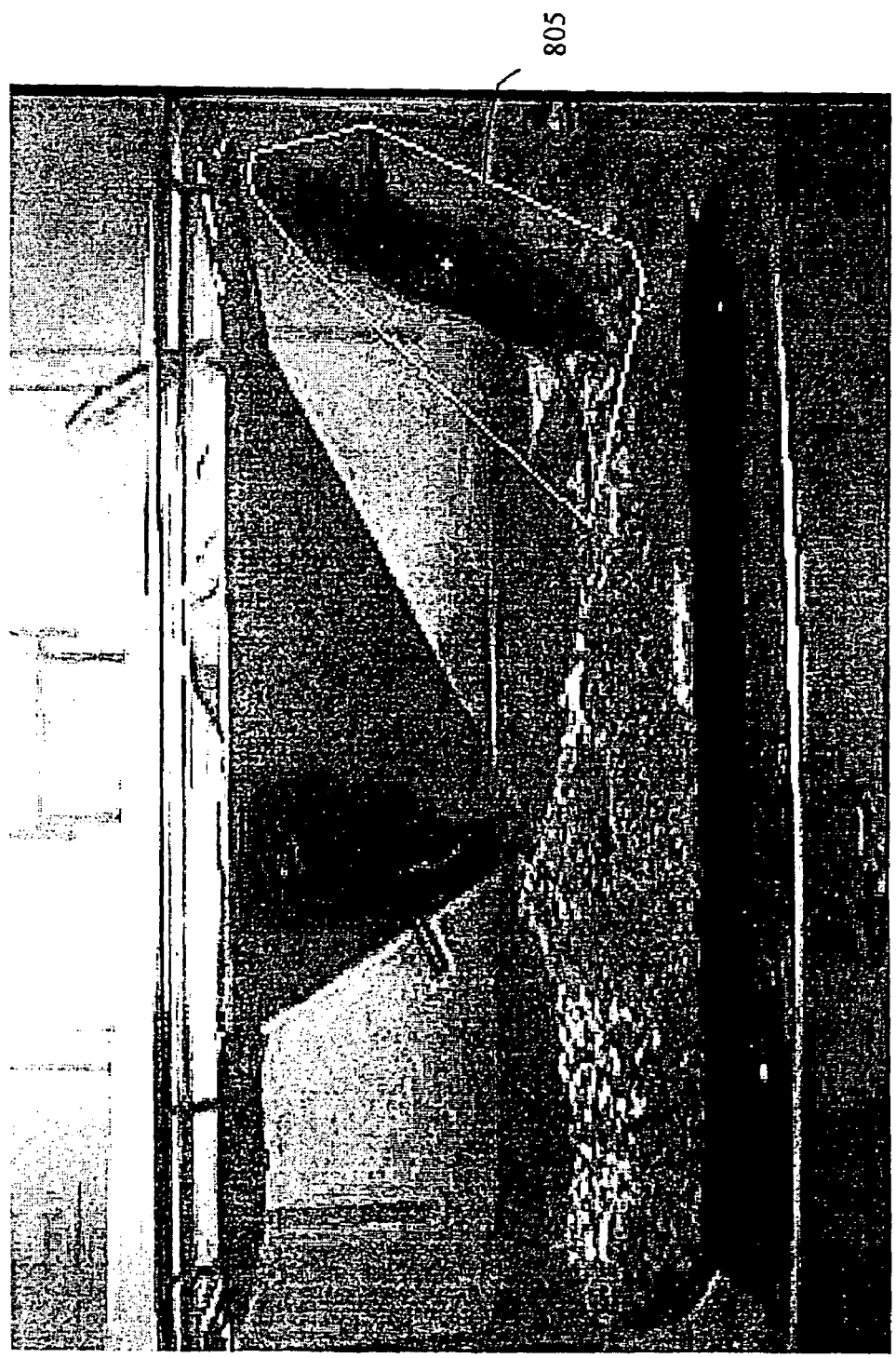
FIG. 8C is a video image frame showing the foreground mouse object correctly identified by the system as identified with a polygon outline, according to one variation of the present invention as applied for monitoring and characterizing mouse behavior.

FIGS. 8A, 8B and 8C illustrate the results of the location and object outline identification for a mouse using the present invention. FIG. 8A illustrates a difference image between foreground and background for the image in FIG. 7A. FIG. 8B illustrates the image after thresholding showing the foreground mouse 705 object correctly identified. FIG. 8C illustrates a video image showing the foreground object, a mouse correctly identified with a polygon outline 805, created using convex hull approach as described above.

Another method of location and outline identification that may improve the representation of the shape of the mouse is the b-spline method. B-spline are piecewise polynomial functions that can provide local approximation of contours of shapes using a small number of parameters and the piecewise smooth lines can be used to represent the outline of the object area. This is useful because human perception of shapes is deemed to be based on curvatures of parts of contours (or object surfaces). This is especially true since shapes of mice are curvatures at any time. This representation may thus results in compression of boundary data as well as smoothing of coarsely digitized contours.

Suppose the mouse shape extracted is represented as a set of ordered boundary points $W_i=(X_i,Y_i)$, with $0 \leq i < n$. This set of points is to be approximated by a B-spline representation as follows:

$$P(t) = \sum_{k=0}^{N-1} Q_k B_k(t)$$

where the $B_k$ are modified B-spline basis functions, and $P(0)=P(N)$ to constitute a close shape. $Q_t \equiv (Q_{1t}, Q_{2t})$ are so called control points, which are not only the coefficients in this equation, but also physically define vertices of a polygon that guides the splines to trace a smooth curve. Using standard Least-square minimization method, to minimize:

$$E = \sum_{i=0}^{n-1} (P_x(t_i) - X_i)^2 + (P_x(t_i) - Y_i)^2$$

where $t_i$ is the knots associated with k where the spline functions are tied together. Two equations can be obtained:

$$\sum_{k=0}^{n-1} M_{i,k} Q_{1t} = \sum_{i=0}^{n-1} B_i(t_j) X_i \quad \sum_{k=0}^{n-1} M_{i,k} Q_{2t} = \sum_{i=0}^{n-1} B_i(t_j) Y_i$$

where $0 \leq i < N$ and $$M_{r,s} = \sum_{k=0}^{n-1} B_r(t_k) B_s(t_k).$$

Based on the silhouette obtained from background subtraction, a series of image processing procedures may be performed first to detect edge using a sobel edge detection algorithm and then, using morphological operations to trim edge points to ensure that the edge points are singly chained.

In order to proceed, a fixed reference point on the closed shape is required. We make use of the features we have extracted for the shape and use the angle, which indicates the direction of the principal axis derived through Principle Component Analysis (CPA), to derive that reference point. A straight line that goes through the centroid with that angle is generated and the point at which this straight line intersects the edge pixel is the reference point. We use the reference point as the starting point to order those edge pixels clockwise to facilitate the solution of the above equations. We obtain a matrix of the control points, which define uniquely the b-spline function.

Figure 9A:
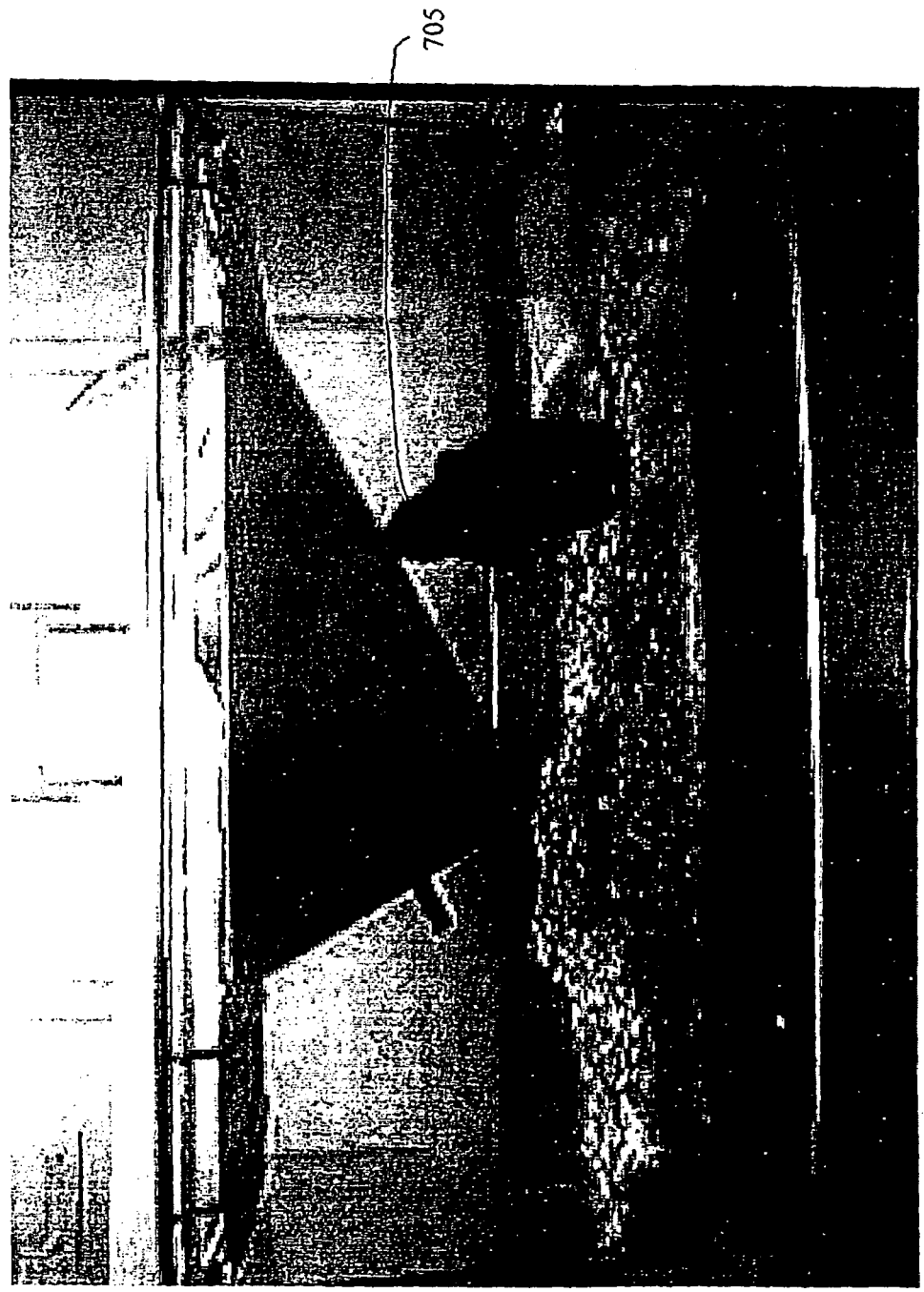
FIG. 9A is a video image frame showing a mouse eating, to demonstrate a b-spline approach to object location and outline identification according to one variation of the present invention as applied for monitoring and characterizing mouse behavior.
Figure 9B:
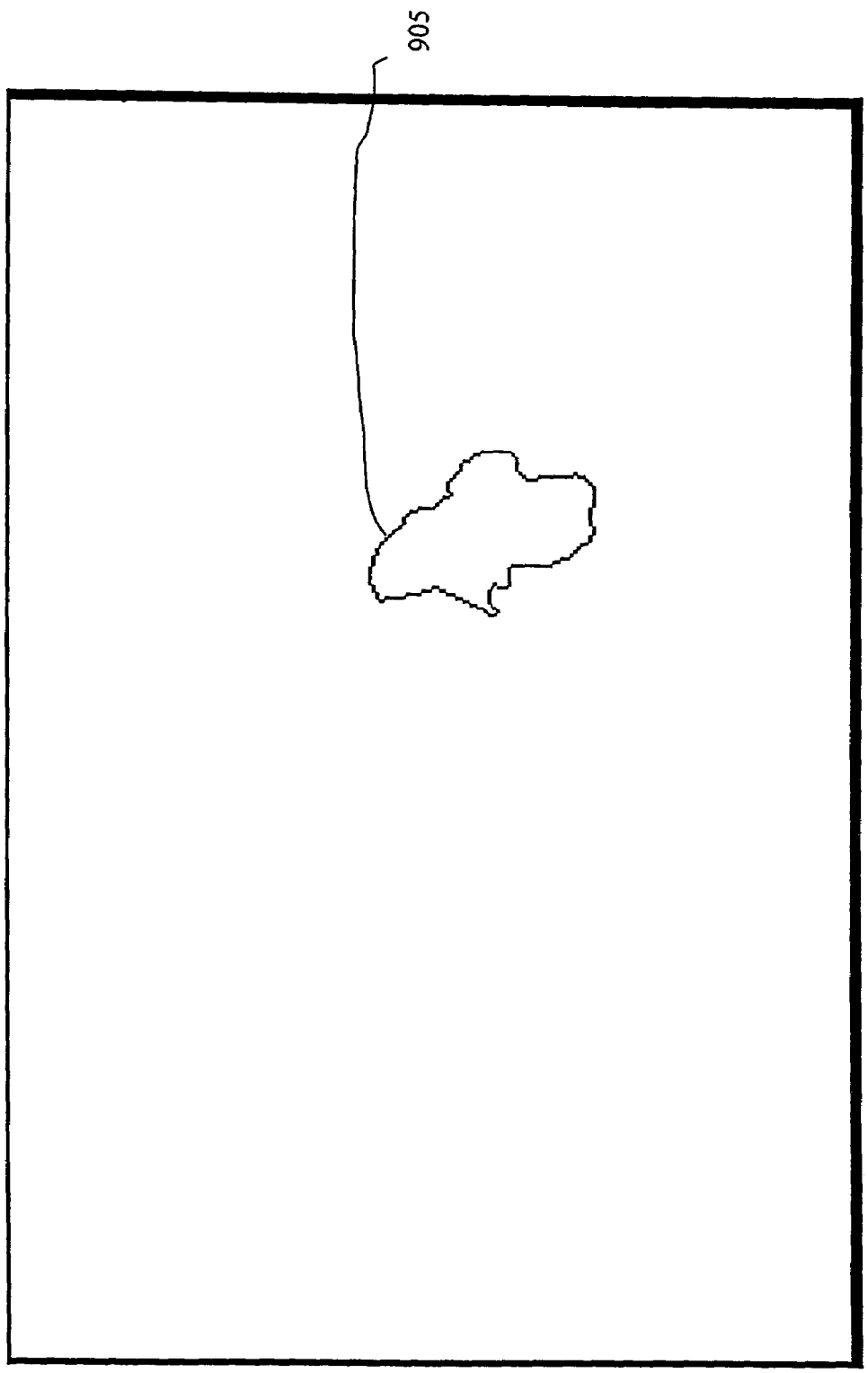
FIG. 9B is a computer generated image showing the outline of the foreground mouse shown in FIG. 9A after edge segmentation, according to one variation of the present invention as applied for monitoring and characterizing mouse behavior.
Figure 9C:
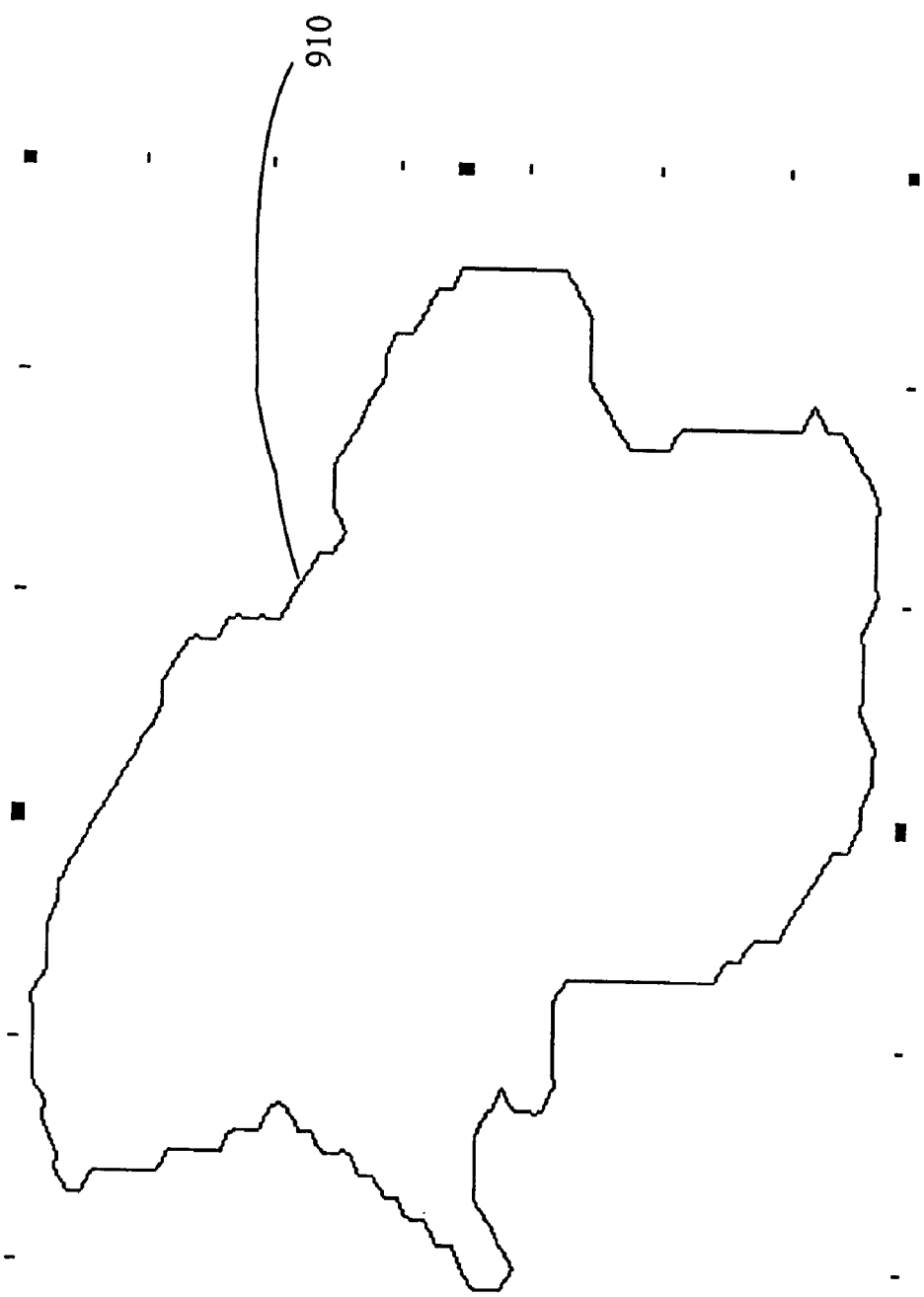
FIG. 9C is a computer generated image of the outline of the foreground mouse shown in FIG. 9A as derived from the outline of the mouse shown in FIG. 9B as generated from a b-spline process, according to one variation of the present invention as applied for monitoring and characterizing mouse behavior.

One example of the use of the B-Spline algorithm implemented in the present invention is illustrated in FIGS. 9A–9C. The original image, the detected edge, and the plotted b-spline function where the vertices of the curve are the control points, are shown in FIGS. 9A, 9B, and 9C, respectively. FIG. 9A illustrates an exemplary video image frame of mouse eating 705. FIG. 9B illustrates the segmented edge 905 of the mouse 705 found in FIG. 9A. FIG. 9C illustrates a b-spline representation of the mouse edge 910 extrapolated from the segmented edge of the mouse found in FIG. 9A.

As a result, either b-spline representation, or convex hull representation can be used as features of foreground object, in addition to other features that include but not limited to: centroid, the principal orientation angle of the object, the area (number of pixels), the eccentricity (roundness), and the aspect ratio of object.

III. Mouse Tracking

Ideal tracking of foreground objects in the image domain involves a matching operation to be performed that identifies corresponding points from one frame to the next. This process may become computationally too consuming or expensive to perform in an efficient manner. Thus, one approach is to use approximations to the ideal case that can be accomplished in a short amount of time. For example, tracking the foreground object may be achieved by merely tracking the outline contour from one frame to the next in the feature space (i.e., identified foreground object image).

In one variation of the invention, tracking is performed in the feature space, which provides a close approximation to tracking in the image domain. The features include the centroid, principal orientation angle of the object, area (number of pixels), eccentricity (roundness), and the aspect ratio of object with lengths measured along the secondary and primary axes of the object. In this case, let S be the set of pixels in the foreground object, A denote the area in number of pixels, $(C_x, C_y)$ denote the centroid, $\phi$ denote the orientation angle, E denote the eccentricity, and R denote the aspect ratio. Then, $$C_x = \frac{1}{A}\sum_S x \quad C_y = \frac{1}{A}\sum_S y$$

Let us define three intermediate terms, called second order moments, $$m_{2,0} = \sum_S (x - C_x)^2 \quad m_{0,2} = \sum_S (y - C_y)^2 \quad m_{1,1} = \sum_S (x - C_x)(y - C_y)$$

Using the central moments, we define, $$\phi = \frac{1}{2}\arctan\frac{2m_{1,1}}{m_{2,0} - m_{0,2}}$$

$$E = \frac{(m_{2,0} - m_{0,2})^2 + 4m_{1,1}^2}{(m_{2,0} + m_{0,2})^2}$$

R is equal to the ratio of the length of the range of the points projected along an axis perpendicular to $\phi$, to the length of the range of the points projected along an axis parallel to $\phi$. This may also be defined as the aspect ratio (ratio of width to length) after rotating the foreground object by $\phi$.

Tracking in the feature space involves following feature values from one frame to the next. For example, if the area steadily increases, it could mean that the mouse is coming out of a cuddled up position to a more elongated position, or that it could be moving from a front view to a side view, etc. If the position of the centroid of the mouse moves up, it means that the mouse may be rearing up on its hind legs. Similarly, if the angle of orientation changes from horizontal to vertical, it may be rearing up. These changes can be analyzed with combinations of features also.

However, it is possible for a b-spline representation to be used to perform near-optimal tracking efficiently in the image domain (i.e., the complete image before background is subtracted).

IV. Mouse Posture Classification

Once the features are obtained for the frames in the video sequence, the foreground state of the mouse is classified into one of the given classes. This involves building a classifier that can classify the shape using the available features. This information may be stored in, for example, a database in, for example, a data memory. In one variation of the invention a Decision Tree classifier (e.g., object shape and posture classifier 215) was implemented by training the classifier with 488 samples of digitized video of a standard, in this case, normal mouse. Six attributes (or features) for each sample were identified. Five posture classes for classification were identified as listed below.

1. Horizontally positioned, side view, either in normal state or elongated.
2. Vertically positioned, either rearing or hanging from top (e.g., See FIGS. 6 and 8C).
3. Cuddled up position (like a ball).
4. Horizontally positioned, but either front or back view, i.e., axis of mouse along the viewer's line of sight.
5. Partially reared, e.g., when drinking or eating, sitting on hind legs (e.g., See FIG. 7A).

The system of the present invention was exercised using these classifications. The distribution of the samples amongst the five classes is shown in Table 1. Performing a 10-fold cross-validation on the 488 training samples, a combined accuracy of 93.65% was obtained indicating that the classifier was performing well. This in the range of the highest levels of agreement between human observers. The cross-validation procedure involves randomly dividing a training set into N approximately equal sets, and for each of the N folds or iterations, one set is set aside for testing while the remaining N−1 sets are used as training samples. Accuracy values for individual classes are indicated in the last column of Table 1. Table 2 shows the overall accuracy values for each fold. We assign appropriate labels for each frame depending on the class to with it was classified to.

TABLE 1

Distribution of samples in the five classes
and the accuracy values for each class.

| Class | Number of Samples | Accuracy (%) |
|---|---|---|
| 1 | 109 | 104/109 = 95.41 |
| 2 | 103 | 103/103 = 100.0 |
| 3 | 106 | 92/106 = 86.79 |
| 4 | 82 | 75/82 = 91.46 |
| 5 | 88 | 83/88 = 94.32 |
| Total | 488 | 457/488 = 93.65 |

It is evident from the data in the Table 1 that class 2 was arguably the most easily for the automated system to identify. This is because the vertical position is quite distinct from the other postures. On the other hand, classes 3 and 4 yield the poorest results due to similarity in the two postures. Both classes depict the mouse as a fairly round object, the only primary difference being the size of the object—class 3 sizes are expected to be slightly larger than those from class 4.

TABLE 2

Accuracy results for each fold
for a cross-validation test.

| Fold | Accuracy |
|---|---|
| 1 | 91.67 |
| 2 | 89.58 |
| 3 | 93.75 |
| 4 | 91.67 |
| 5 | 95.83 |
| 6 | 95.83 |
| 7 | 93.75 |
| 8 | 97.92 |
| 9 | 95.83 |
| 10 | 91.07 |
| Overall | 93.65 |

As illustrated by the tables, the present system provides good accuracy for mouse shape and posture recognition and classification.

V. Behavior identification

Once the postures in all the frames in the video clip have been labeled, we now need to determine certain pre-defined behaviors as defined in the database based on the postures that have been identified. Currently, 23 such behaviors have been defined which include: sleep, groom, eat, rear up on the hind legs, drink, walk, jump, hang from the top of the cage, stretch, dig, awaken, arousal, twitch, stretch, yawn, pause, circle, forage, chew, urinate, defecate. In addition, grooming is divided into licking and scratching and rearing up into supported and unsupported.

This process will be accomplished in real-time so that immediate results will be reported to investigators or stored in a database. One approach is to use a rule-based label analysis procedure (or a token parsing procedure) by which the sequence of labels is analyzed and identify particular behaviors when its corresponding sequence of labels is derived from a video frame being analyzed. For example, if a long sequence (lasting for example several minutes) of the "Cuddled up position" label (Class 3) is observed, and if its centroid remains stationary, then, it may be concluded that the mouse is sleeping. If the location of the waterspout is identified, and if we observe a series of "partially reared" (Class 5) labels, and if the position of the centroid, and the mouse's angle of orientation fall within a small range that has been predetermined, the system can determine and identify that the mouse is drinking. It may also be useful for certain extra conditions to be tested such as, "some part (the mouth) of the mouse must touch the spout if drinking is to be identified" in addition to temporal characteristics of the behavior.

Another approach involves using a probabilistic model such as Hidden Markov Models (HMMs), where models may be built for each class of behavior with training samples. These models may then be used to identify behaviors based on the incoming sequence of labels. The HMM can provide significant added accuracy to temporal relationships for proper complex behavior characterization.

Figure 10:
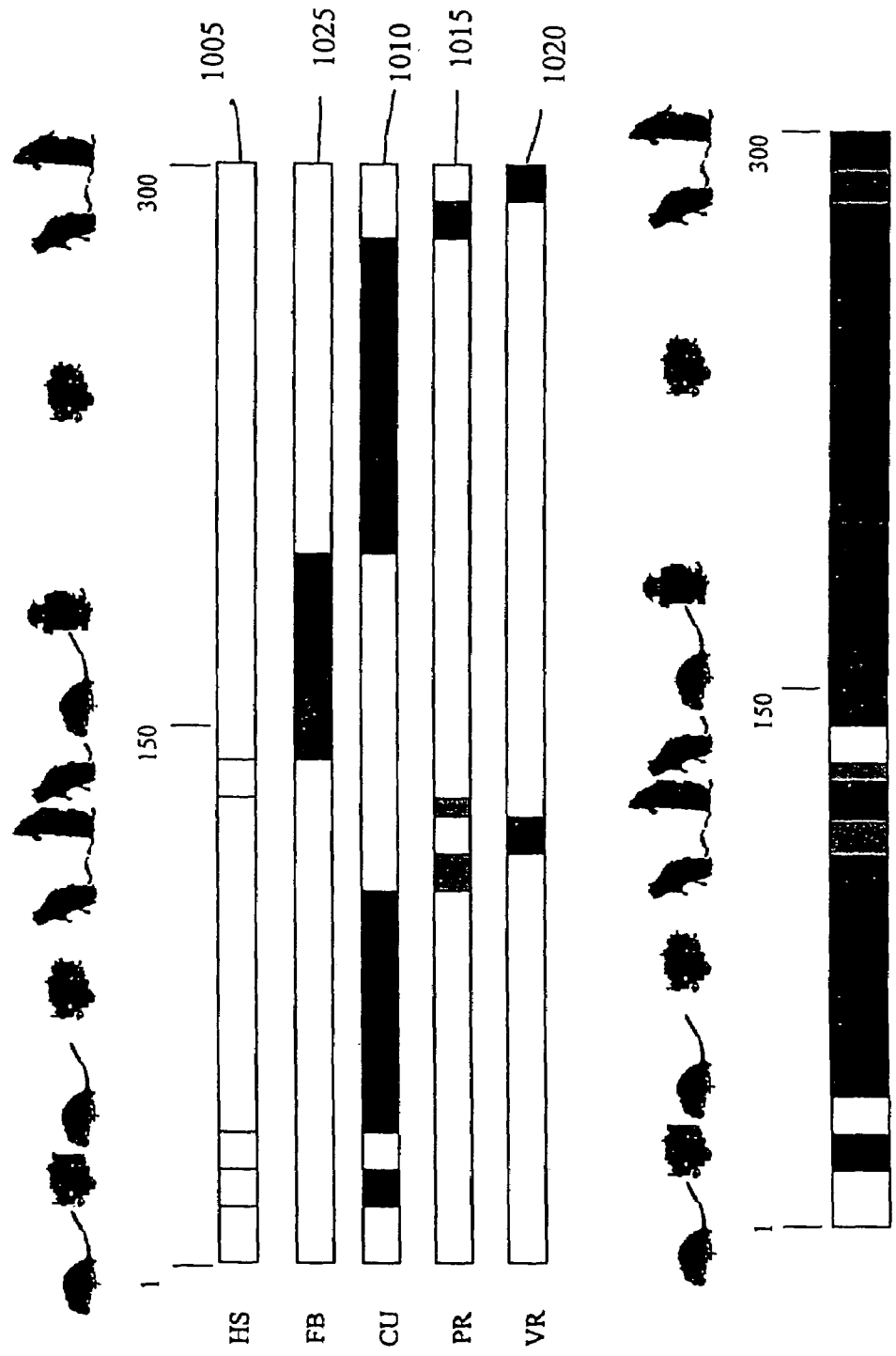
FIG. 10 is a chart illustrating one example of various mouse state transitions used in characterizing mouse behavior including: Horizontal (HS); Cuddled up (CU); Partially reared (PR); Vertically Reared (VR); and Forward Back (FB), along with an indication of duration of these states based on a sample, according to one variation of the present invention, as applied for monitoring and characterizing mouse behavior.

Referring now to FIG. 10, various exemplary mouse state transitions tested in the present invention are illustrated. The five exemplary mouse state transitions include: (1) Horizontal (HS) 1005, (2) Cuddled up (CU) 1010, (3) Partially reared (PR) 1015, (4) Vertically Reared (VR) 1020, and (5) Forward Back (FB) 1025 postures. As illustrated, FIG. 10 shows the five posture states and the duration for which a mouse spent in each state in an exemplary sample video clip. One example of a pattern that is understandable and evident from the figure is that the mouse usually passes through the partially reared (PR) 1015 state to reach the vertically reared (VR) 1025 state from the other three ground-level states. The states are defined according to the five posture classes mentioned previously.

Many important features can be derived from this representation, e.g., if the state changes are very frequent, it would imply that the mouse is very active. If the mouse remained in a single ground-level state such as "cuddled-up" (class 3) for an extended period of time, the system may conclude that the mouse is sleeping or resting. The sequence of transitions are also important, e.g., if the mouse rears (class 2) from a ground-level state such as "Horizontally positioned" (class 1), it should pass briefly through the partially reared state (class 5). Techniques such as HMMs exploit these types of time-sequence-dependent information for performing classification.

A simple HMM system has been created using dynamic programming to find the best match between the input sequence and paths through the state machine. It has been used to classify events in one of the mouse behavior sequences. The HMM system was provided with a sequence of tokens representing recognized actions or views from a benchmark mouse-rear video; this file includes views from five different postures, which are:

c=cuddled_posture_view f=front_or_back_view h=horizontal_side_view p=partially_reared_view r=reared_or_vertical_view  (1)

Each of these represents a posture of the mouse and all together they constitute five (5) tokens. These tokens cause the HMM to go from one (hidden) state to another. The HMM may classify behavior into one of, for example, four hidden states: horizontal, rearing, cuddled, or indecisive:

0=horizontal; 1=cuddled; 2=rearing; 3=indecisive;  (2)

Thus, the HMM defining mouse behaviors can be described as:

size 4 5; start 0 stop 0; symbols c f h p r

This approach to a HMM for mouse behavior characterization may result in a number of mismatched cases which may be categorized into three (3) types: (a) one mismatch (the last token) because the start and stop states were forced to be 0; (b) the PARTIALLY_REARED may be mapped to indecisive, but this may only be a difference in the naming; and (c) the FRONT_OR_BACK may be mapped to the same value as HORIZ_SIDE_VIEW (21 cases). However, it is reasonable that both FRONT_OR_BACK and HORIZ_SIDE_VIEW are mapped to the same classification because both are similar to each other "behaviorally", i.e., from the mouse's point of view, being FRONT_OR_BACK or HORIZ_SIDE are the same thing. This may yield a perfect mapping from input to output. This is but one exemplary approach for the frame work for defining a HMM analysis for determining mouse behavior.

Although the above exemplary embodiment is directed to a mouse analyzed in a home cage, it is to be understood that the mouse (or any object) may be analyzed in any location or environment. Further, the invention in one variation may be used to automatically detect and characterize one or more particular behaviors. For example, the system could be configured to automatically detect and characterize an animal freezing and/or touching or sniffing a particular object. Also, the system could be configured to compare the object's behavior against a "norm" for a particular behavioral parameter. Other detailed activities such as skilled reaching and forelimb movements as well as social behavior among groups of animals can also be detected and characterized.

In summary, when a new video clip is analyzed, the system of the present invention first obtains the video image background and uses it to identify the foreground objects. Then, features are extracted from the foreground objects, which are in turn passed to the decision tree classifier for classification and labeling. This labeled sequence is passed to a behavior identification system module that identifies the final set of behaviors for the video clip. The image resolution of the system that has been obtained and the accuracy of identification of the behaviors attempted so far have been very good and resulted in an effective automated video image object recognition and behavior characterization system.

The invention may identify some abnormal behavior by using video image information (for example, stored in memory) of known abnormal animals to build a video profile for that behavior. For example, video image of vertical spinning while hanging from the cage top was stored to memory and used to automatically identify such activity in mice. Further, abnormalities may also result from an increase in any particular type of normal behavior. Detection of such new abnormal behaviors may be achieved by the present invention detecting, for example, segments of behavior that do not fit the standard profile. The standard profile may be developed for a particular strain of mouse whereas detection of abnormal amounts of a normal behavior can be detected by comparison to the statistical properties of the standard profile. Thus, the automated analysis of the present invention may be used to build a profile of the behaviors, their amount, duration, and daily cycle for each animal, for example each commonly used strain of mice. A plurality of such profiles may be stored in, for example, a database in a data memory of the computer. One or more of these profile may then be compared to a mouse in question and difference from the profile expressed quantitatively.

The techniques developed with the present invention for automation of the categorization and quantification of all home-cage of mouse behaviors throughout the daily cycle is a powerful tool for detecting phenotypic effects of gene manipulations in mice. As previously discussed, this technology is extendable to other behavior studies of animals and humans, as well as surveillance purposes. In any case, the present invention has proven to be a significant achievement in creating an automated system and methods for automated accurate identification, tracking and behavior categorization of an object whose image is captured in a video image.

Although particular embodiments of the present invention have been shown and described, it will be understood that it is not intended to limit the invention to the preferred or disclosed embodiments, and it will be obvious to those skilled in the art that various changes and modifications may be made without departing from the spirit and scope of the present invention. Thus, the invention is intended to cover alternatives, modifications, and equivalents, which may be included within the spirit and scope of the invention as defined by the claims.

For example, the present invention may also include audio analysis and/or multiple camera analysis. The video image analysis may be augmented with audio analysis since audio is typically included with most video systems today. As such, audio may be an additional variable used to determine and classify a particular objects behavior. Further, in another variation, the analysis may be expanded to video image analysis of multiple objects, for example mice, and their social interaction with one another. In a still further variation, the system may include multiple cameras providing one or more planes of view of an object to be analyzed. In an even further variation, the camera may be located in remote locations and the video images sent via the Internet for analysis by a server at another site. In fact, the standard object behavior data and/or database may be housed in a remote location and the data files may be downloaded to a stand alone analysis system via the Internet, in accordance with the present invention. These additional features/functions adds versatility to the present invention and may improve the behavior characterization capabilities of the present invention to thereby achieve object behavior categorization which is nearly perfect to that of a human observer for a broad spectrum of applications.

All publications, patents, and patent applications cited herein are hereby incorporated by reference in their entirety for all purposes.

What is claimed is:

1. A device comprising:
  a first module configured to receive video images and to identify objects of interest in response to the video images;
  a second module coupled to the first module and configured to classify a plurality of shape and posture categories based on a plurality of observed states of the objects of interest; and
  a third module coupled to the second module, wherein the third module is configured to identify behaviors of the objects of interest using the plurality of shape and posture categories and standard object behaviors, and is further configured to analyze temporal ordering of behavior primitives time-series analysis to indentify a transition from a previous behavior primitive to a next behavior primitive.

2. The device of claim 1, wherein the second module further obtains feature information by tracking the objects of interest over a plurality of video images.

3. The device of claim 2, wherein the third module is further configured to identify behaviors of the objects of interest by comparing feature information of the objects of interest with predefined categories exhibited by the standard object behaviors.

4. The device of claim 2, wherein the third module is further configured to identify at least one of eating, rearing, jumping, drinking, running, walking, chewing, grooming, hanging, cuddling, landing vertically, repetitively jumping, circling, sleeping, twitching, awakening, digging, foraging, sniffing, pausing, urinating, stretching, licking, scratching, spinning, sitting, standing, and lying.

5. The device of claim 1, wherein the first module is an object identification and segregation module that identifies and segregates predetermined types of objects from the video images.

6. The device of claim 5, wherein the second module further includes:
an object tracking module configured to track the objects of interest in a series of video image frames; and
an object shape and posture classifier coupled to the object tracking module and configured to provide the plurality of shape and posture categories.

7. The device of claim 6, wherein the third module includes a behavior identification module, which is coupled to a standard object behavior storage module.

8. A system for characterizing activity of objects comprising:
a video camera;
a video digitization unit; and
a digital processing unit that includes:
a device of claim 1; and
a memory device.

9. A method of characterizing an activity comprising:
obtaining a stream of video image frames from a monitoring device;
identifying objects of interest from the stream of video image frames;
providing feature information of the objects of interest in response to the stream of video image frames;
classifying postures of the objects of interest in response to the feature information;
obtaining standard object behaviors from a storage memory device; and
characterizing behaviors of the objects of interest in response to a comparison between the postures of the objects of interest and the standard object behaviors, wherein the characterizing the behaviors of the objects of interest further includes analyzing temporal ordering of behavior primitive using time-series analysis to identify a transition from a previous behavior primitive to a next behavior primitive.

10. The method of claim 9, wherein the time-series analysis further includes employing Hidden Markov Models (HMMs).

11. The method of claim 9, wherein the providing feature information further includes tracking physical changes of the objects of interest over multiple video image frames.

12. The method of claim 9, wherein the identifying objects of interest from the stream of video image frames further includes detecting foreground objects of interest from the video image frames.

13. The method of claim 12, wherein the detecting foreground objects of interest further includes subtracting a background utilizing a background subtraction algorithm.

14. The method of claim 9, wherein the identifying objects of interest further includes identifying humans, vehicles, and other moving and non-moving objects.

15. The method of claim 9, wherein the identifying objects of interest further includes identifying an animal.

16. The method of claim 15, wherein the identifying an animal further includes identifying a biological mouse or rat.

17. The method of claim 9, wherein the classifying postures of the objects of interest further includes:
describing a sequence of postures as behavior primitives; and
aggregating behavior primitives to identify behaviors of the objects of interest over a plurality of video image frames.

18. The method of claim 17, wherein the classifying of postures of the objects of interest includes detecting the shapes of the objects of interest.

19. The method of claim 9, wherein the characterizing the behaviors of the objects of interest further includes identifying one of eating, rearing, jumping, drinking, running, walking, chewing, grooming, hanging, cuddling, landing vertically, repetitively jumping, circling, sleeping, twitching, awakening, digging, foraging, sniffing, pausing, urinating, stretching, licking, scratching, spinning, sitting, standing, and lying.

20. The method of claim 9, wherein the identifying an objects of interest further includes detecting one of vertical position side view, horizontal position side view, vertical position front view, horizontal position front view, and moving of the objects of interest.

21. An apparatus for characterizing an activity comprising:
means for obtaining a stream of video image frames from a monitoring device;
means for identifying objects of interest from the stream of video image frames;
means for providing feature information of the objects of interest in response to the stream of video image frames;
means for classifying postures of the objects of interest in response to the feature information;
means for obtaining standard object behaviors from a storage memory device; and
means for characterizing behaviors of the objects of interest in response to comparison between the postures of the objects of interest and the standard object behaviors; wherein the means for characterizing further includes means for analyzing temporal ordering of behavior primitives using transitional information from a previous behavior primitive to a next behavior primitive; wherein the means for analyzing temporal ordering of behavior primitives further includes means for utilizing Hidden Markov Model time-series analysis.

22. The apparatus of claim 21, wherein the means for providing feature information further includes means for tracking physical changes of the objects of interest over multiple video image frames.

23. The apparatus of claim 21, wherein the means for identifying objects of interest from the stream of video image frames further includes means for detecting foreground objects of interest from the video image frames.

24. The apparatus of claim 23, wherein the means for detecting foreground objects of interest further includes means for subtracting a background utilizing a background subtraction algorithm.

25. The apparatus of claim 21, wherein the means for identifying objects of interest further includes means for identifying humans, vehicles, and other moving and non-moving objects.

26. The apparatus of claim 21, wherein the means for identifying objects of interest further includes means for identifying an animal.

27. The apparatus of claim 26, wherein the means for identifying an animal further includes means for identifying a biological mouse or rat.

28. The apparatus of claim 21, wherein the means for classifying postures of the objects of interest further includes:

means for describing a sequence of postures as behavior primitives; and means for aggregating behavior primitives to identify behaviors of the objects of interest over a plurality of video image frames.

29. The apparatus of claim 28, wherein the means for classifying of postures of the objects of interest includes means for detecting shapes of the objects of interest.

30. The apparatus of claim 21, wherein the means for characterizing the behaviors of the objects of interest further includes means for identifying one of eating, rearing, jumping, drinking, running, walking, chewing, grooming, hanging, cuddling, landing vertically, repetitively jumping, circling, sleeping, twitching, awakening, digging, foraging, sniffing, pausing, urinating, stretching, licking, scratching, spinning, sitting, standing, and lying.

31. The apparatus of claim 21, wherein the means for identifying objects of interest further includes means for detecting one of vertical position side view, horizontal position side view, vertical position front view, horizontal position front view, and moving of the objects of interest.

32. A machine-readable medium having stored thereon computer executable instructions, which cause a digital processing system to perform a function, the function comprising:

obtaining a stream of video image frames from a monitoring device;

identifying objects of interest from the stream of video image frames;

providing feature information of the objects of interest in response to the stream of video image frames;

classifying postures of the objects of interest in response to the feature information;

obtaining standard object behaviors from a storage memory device; and characterizing behaviors of the objects of interest in response to comparison between the postures of the objects of interest and the standard object behaviors, wherein the characterizing the behaviors of the objects of interest further includes analyzing temporal ordering of behavior primitives.

33. The machine-readable medium of claim 32, wherein the analyzing temporal ordering of the behavior primitives further includes utilizing time-series analysis to identify a transition from a previous behavior primitive to a next behavior primitive.

34. The machine-readable medium of claim 33, wherein the time-series analysis further includes employing Hidden Markov Models (HMMs).

35. The machine-readable medium of claim 32, wherein the providing feature information further includes tracking physical changes of the objects of interest over multiple video image frames.

36. The machine-readable medium of claim 32, wherein the identifying objects of interest from the stream of video image frames further includes detecting foreground objects of interest from the video image frames.

37. The machine-readable medium of claim 36, wherein the detecting foreground objects of interest further includes subtracting a background utilizing a background subtraction algorithm.

* * * * *

UNITED STATES PATENT AND TRADEMARK OFFICE
CERTIFICATE OF CORRECTION

| | |
|---|---|
| PATENT NO. | : 7,068,842 B2 |
| APPLICATION NO. | : 10/666741 |
| DATED | : June 27, 2006 |
| INVENTOR(S) | : Liang et al. |

It is certified that error appears in the above-identified patent and that said Letters Patent is hereby corrected as shown below:

Column 24, line 65, in the phrase "behavior primitives time-series analysis to indentify a transition," insert word --using-- between words "primitives" and "time-series," and delete word "indentify" and insert word --identify-- in its place.

Column 25, line 5, in the phrase "of behavior primitive using time-series analysis to identify a transition", delete word "primitive" and insert word --primitives-- in its place.

Signed and Sealed this

Nineteenth Day of September, 2006

JON W. DUDAS
*Director of the United States Patent and Trademark Office*